US012586568B2

(12) United States Patent
Laufer et al.

(10) Patent No.:     US 12,586,568 B2
(45) Date of Patent:       Mar. 24, 2026

(54) SYNTHETICALLY GENERATING INNER SPEECH TRAINING DATA

(71) Applicant: Snap Inc., Santa Monica, CA (US)

(72) Inventors: Yaron Laufer, Brookline, MA (US);
Meir Meshulam, Princeton, NJ (US);
Assif Ziv, Beit Yitzhak-Sha'ar Hefer
(IL)

(73) Assignee: SNAP INC., Santa Monica, CA (US)

( * ) Notice: Subject to any disclaimer, the term of this
patent is extended or adjusted under 35
U.S.C. 154(b) by 275 days.

(21) Appl. No.: 18/484,282

(22) Filed: Oct. 10, 2023

(65) Prior Publication Data

US 2025/0118290 A1      Apr. 10, 2025

(51) Int. Cl.
*G10L 15/06*          (2013.01)
*A61B 5/394*        (2021.01)
*G10L 15/24*          (2013.01)
*G10L 21/16*          (2013.01)
*G10L 25/78*          (2013.01)

(52) U.S. Cl.
CPC ............ *G10L 15/063* (2013.01); *A61B 5/394*
(2021.01); *G10L 15/24* (2013.01); *G10L 21/16*
(2013.01); *G10L 25/78* (2013.01); *G10L*
*2015/0635* (2013.01)

(58) Field of Classification Search
None
See application file for complete search history.

(56) References Cited

U.S. PATENT DOCUMENTS 10,621,973  B1 *   4/2020   McVicker ................ H04R 1/14
12,105,876  B2   10/2024   Garg et al.

2003/0163306  A1     8/2003   Manabe et al.
2019/0074012  A1 *   3/2019   Kapur .................... A61B 5/682
2023/0215437  A1 *   7/2023   Maizels ............. G02B 27/0093
                                                                         704/235
2024/0220811  A1     7/2024   Garg et al.
2024/0221718  A1     7/2024   Kothari et al.
(Continued)

OTHER PUBLICATIONS

Rekrut, Maurice, Abdulrahman Mohamed Selim, and Antonio Krüger.
"Improving silent speech bci training procedures through transfer
from overt to silent speech." 2022 IEEE International Conference
on Systems, Man, and Cybernetics (SMC). IEEE, 2022. (Year:
2022).*

(Continued)

*Primary Examiner* — Shaun Roberts
(74) *Attorney, Agent, or Firm* — SCHWEGMAN
LUNDBERG & WOESSNER, P.A.

(57)                 ABSTRACT

Methods and systems are disclosed for synthetically gener-
ating inner speech training data. The methods and systems
access a collection of overt speech signals representing
phonemes, phoneme sounds, words or phrases spoken at
least partially using overt speech. The methods and systems
transform the collection of overt speech signals into inner
speech training data comprising electromyograph (EMG)
data representing inner speech corresponding to the pho-
nemes, phoneme sounds, words or phrases spoken at least
partially using the overt speech. The methods and systems
train a machine learning model to decode inner speech
signals into a set of corresponding phonemes, phoneme
sounds, words or phrases based on the inner speech training
data.

20 Claims, 11 Drawing Sheets

(56)                    References Cited

U.S. PATENT DOCUMENTS

| | | |
|---|---|---|
| 2024/0221719 A1 | 7/2024 | Kothari et al. |
| 2024/0221738 A1 | 7/2024 | Garg et al. |
| 2024/0221741 A1 | 7/2024 | Kothari et al. |
| 2024/0221751 A1 | 7/2024 | Garg et al. |
| 2024/0221753 A1 | 7/2024 | Garg et al. |
| 2024/0221762 A1 | 7/2024 | Garg et al. |
| 2024/0296833 A1 | 9/2024 | Garg et al. |
| 2025/0061896 A1* | 2/2025 | Shires .................... G10L 17/00 |

OTHER PUBLICATIONS

"International Application Serial No. PCT/US2024/049637, International Search Report mailed Dec. 11, 2024", 3 pgs.
"International Application Serial No. PCT/US2024/049637, Written Opinion mailed Dec. 11, 2024", 6 pgs.
Bradley, J Betts, et al., "Small-vocabulary speech recognition using surface electromyography", Interacting With Computers 18, Butterworth-Heinemann, GB, (Dec. 1, 2006), 1242-1259.
Kapur, Arnav, "AlterEgo a Personalized Wearable Silent Speech Interface", IUI 2018 Session 1B Multimodal Interfaces, (Mar. 7, 2018), 10 pgs.
"FOOOF—fitting oscillations & one over f", [Online]. Retrieved from the Internet: <URL: https://web.archive.org/web/20230101172053/https://fooof-tools.github.io/fooof/>, (Archived on Jan. 1, 2023), 9 pgs.

* cited by examiner 104             124                  100

Figure 2:
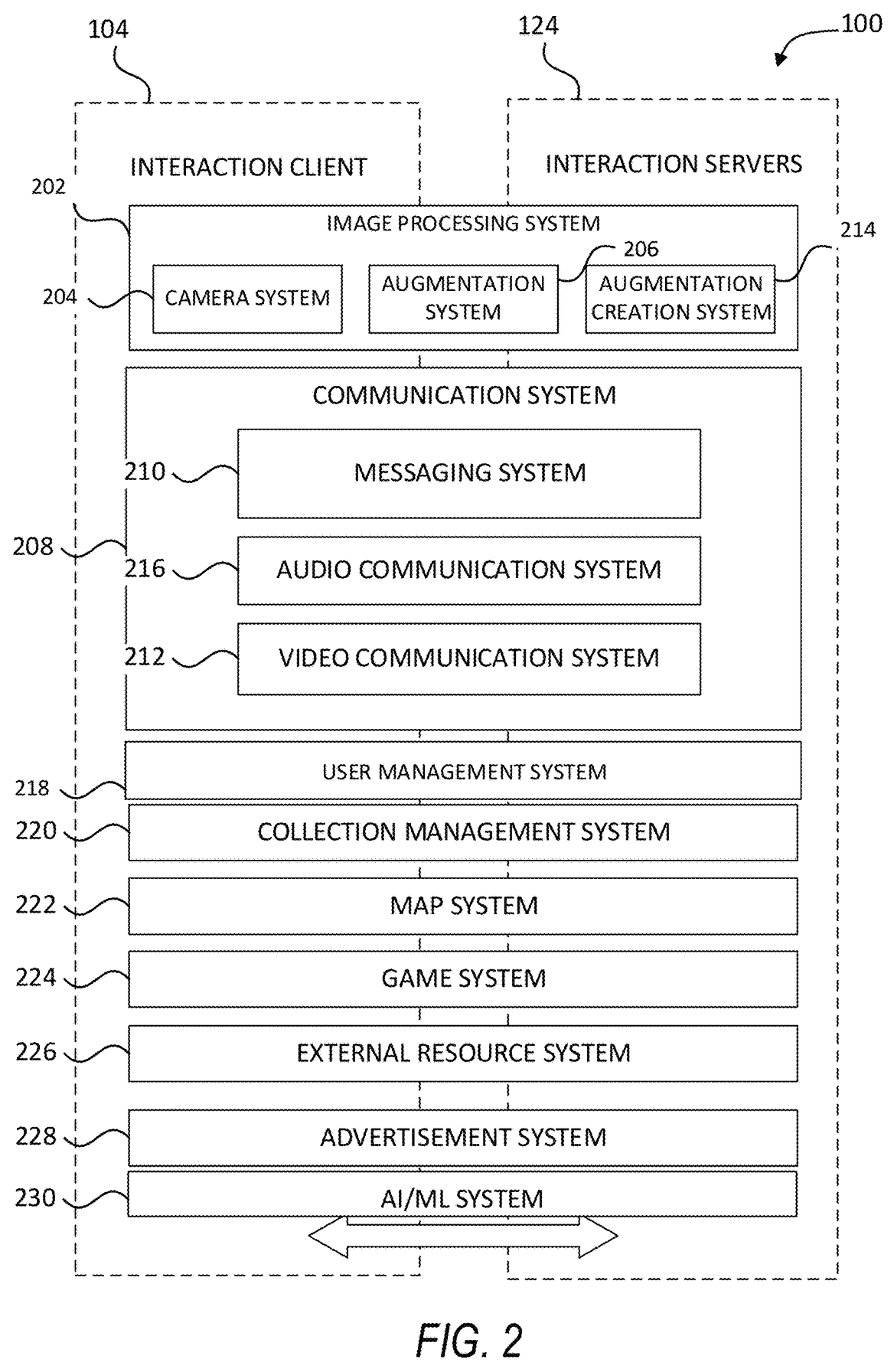

INTERACTION CLIENT        INTERACTION SERVERS

202

IMAGE PROCESSING SYSTEM       214

206

204    CAMERA SYSTEM     AUGMENTATION SYSTEM     AUGMENTATION CREATION SYSTEM

COMMUNICATION SYSTEM

208

210    MESSAGING SYSTEM

216    AUDIO COMMUNICATION SYSTEM

212    VIDEO COMMUNICATION SYSTEM

218    USER MANAGEMENT SYSTEM

220    COLLECTION MANAGEMENT SYSTEM

222    MAP SYSTEM

224    GAME SYSTEM

226    EXTERNAL RESOURCE SYSTEM

228    ADVERTISEMENT SYSTEM

230    AI/ML SYSTEM

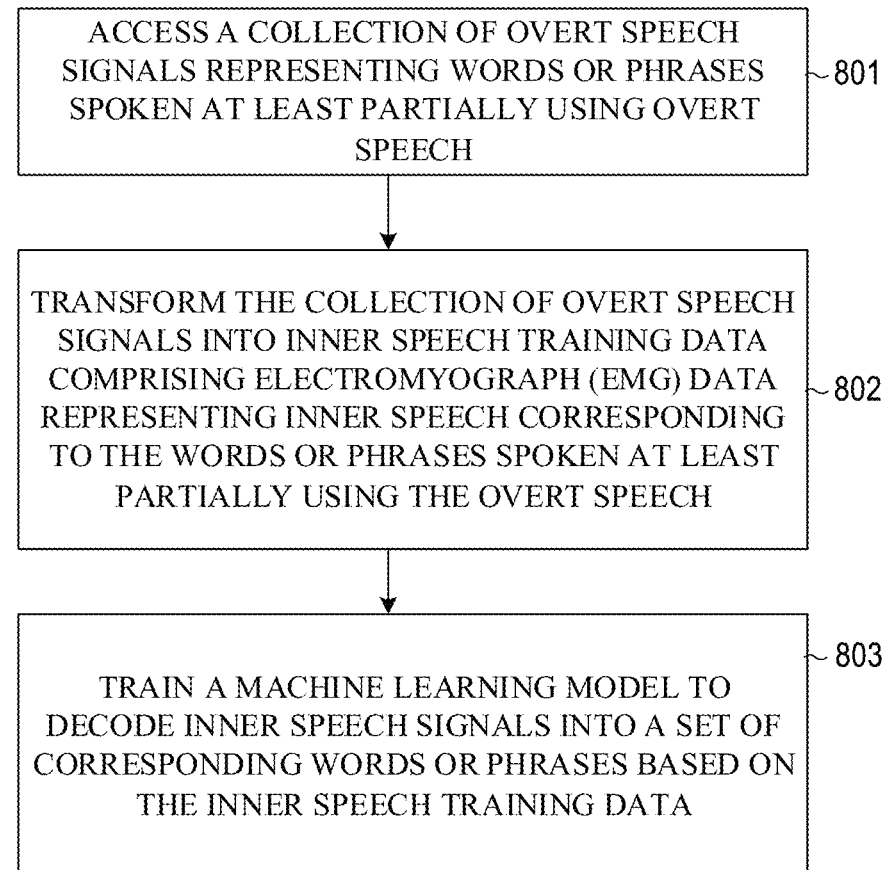

ACCESS A COLLECTION OF OVERT SPEECH SIGNALS REPRESENTING WORDS OR PHRASES SPOKEN AT LEAST PARTIALLY USING OVERT SPEECH ~801

TRANSFORM THE COLLECTION OF OVERT SPEECH SIGNALS INTO INNER SPEECH TRAINING DATA COMPRISING ELECTROMYOGRAPH (EMG) DATA REPRESENTING INNER SPEECH CORRESPONDING TO THE WORDS OR PHRASES SPOKEN AT LEAST PARTIALLY USING THE OVERT SPEECH ~802

TRAIN A MACHINE LEARNING MODEL TO DECODE INNER SPEECH SIGNALS INTO A SET OF CORRESPONDING WORDS OR PHRASES BASED ON THE INNER SPEECH TRAINING DATA ~803

FIG. 8

SYNTHETICALLY GENERATING INNER SPEECH TRAINING DATA

TECHNICAL FIELD

The present disclosure relates to electromyograph (EMG) speech systems and to interaction applications and/or extended reality (XR) devices, such as augmented reality (AR) and/or virtual reality (VR) devices.

BACKGROUND

Some electronics-enabled devices include various input interfaces to allow a user to communicate with other users. Such input interfaces include voice message interfaces that enable users to send verbal messages to others. Other input interfaces include textual input in which a user types in their desired message. These types of input interfaces require movement by users, such as moving facial muscles to produce speech for verbal messages or moving fingers to select different keys on a keyboard.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some nonlimiting examples are illustrated in the figures of the accompanying drawings in which:

FIG. 2 is a diagrammatic representation of a messaging system that has both client-side and server-side functionality, according to some examples.

FIG. 8 is a flowchart illustrating example operations of the EMG speech detection system, according to some examples.

DETAILED DESCRIPTION

Figure 1:
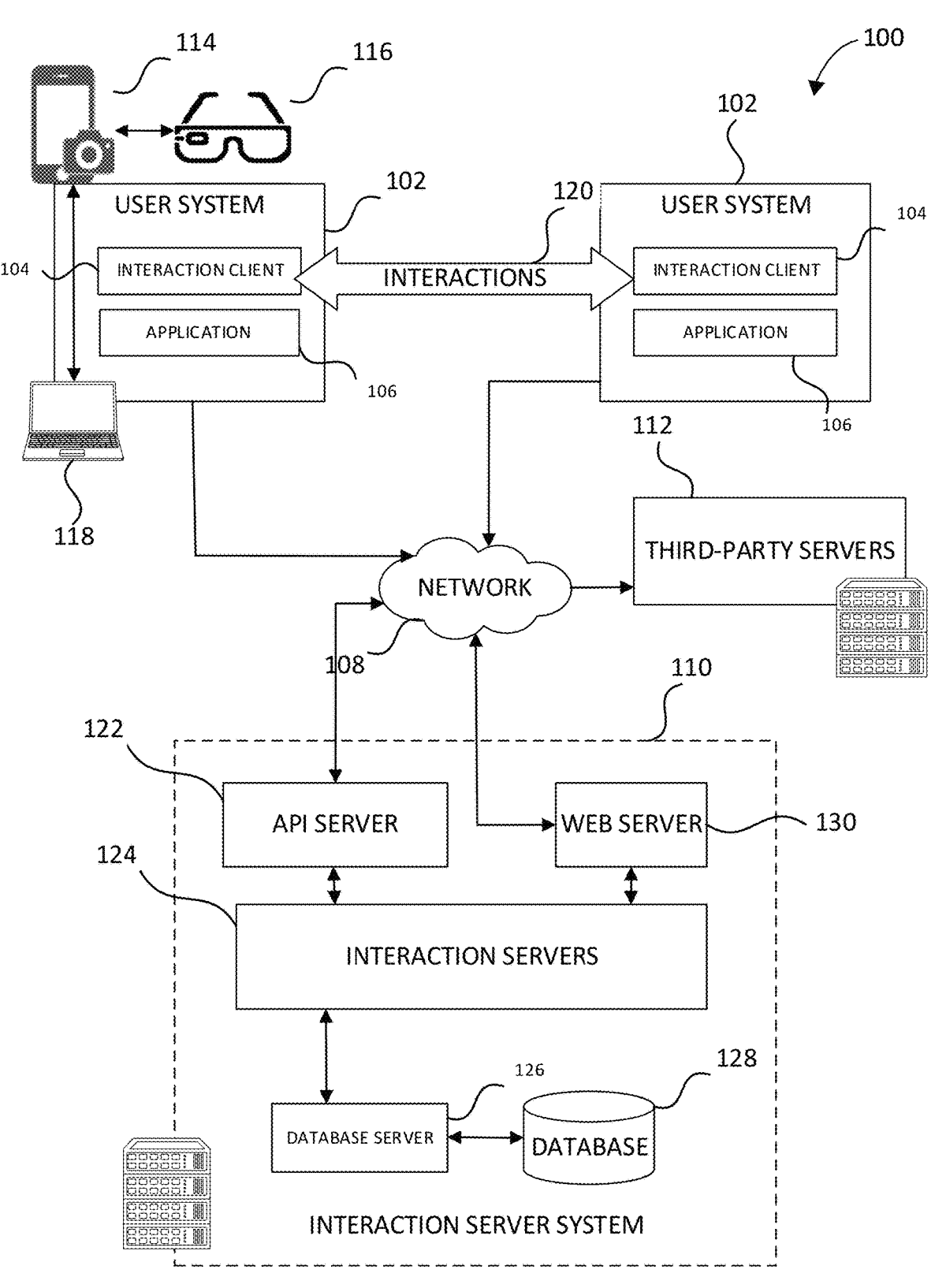
FIG. 1 is a diagrammatic representation of a networked environment in which the present disclosure may be deployed, according to some examples.

The description that follows includes systems, methods, techniques, instruction sequences, and computing machine program products that embody illustrative examples of the disclosure. In the following description, for the purposes of explanation, numerous specific details are set forth in order to provide an understanding of various examples. It will be evident, however, to those skilled in the art, that examples may be practiced without these specific details. In general, well-known instruction instances, protocols, structures, and techniques are not necessarily shown in detail.

Some conventional noninvasive brain-computer interfaces (BCI) use electroencephalography (EEG) sensors. Such systems detect neural signals in the brain of a user and decode the neural signals into various operations. These systems can be cumbersome to deploy and difficult to place on a user's head accurately. Other noninvasive computer interfaces leverage EMG electrodes, which detect electrical signals associated with muscle activity. Such systems rely on measurement of muscle activity (as captured by EMG signals). Of particular interest to BCI is the use of surface EMG to discriminate and recognize subaudible speech signals produced with relatively little or no acoustic input. Speech-related EMG signals can be measured in various locations across the face and neck, including on the side of a subject's throat, near the larynx, and under the chin.

Speaking is a motor activity associated with overt muscle movement, but thinking about speech is not a motor activity. Inner speech or imaginary speech refers to the voluntary act of saying something silently, such as vividly imagining speaking, with no or minimal movement of the tongue, mouth, and/or facial muscles, and without aiming to be understood by another person. Specifically, when a person intends to speak a word or phrase, the person's brain generates a neural signal and provides that neural signal to the corresponding speech-producing muscles, such as the larynx, throat, tongue, and so forth. Subthreshold muscle activation (also referred to as subthreshold muscle activity (STA)) is a phenomenon that occurs when a person performs inner speech (or other muscle movement) by imagining a motor activity or giving attention to another human movement while focusing on specific phonemes, phoneme sounds, words or phrases or actions. In such cases, the brain's motor cortex (M1) sends a neural signal to the relevant muscles. The signal is too subtle to fully activate the muscle; however, the signal can be detected by EMG electrodes. The EMG signal may carry information that is not readily decoded from the EEG signal and/or have a better signal-to-noise ratio, which makes it easier to record and pick up using surface electrodes, potentially resulting in improved decoding of intended operations.

Users are always seeking new ways to communicate with others and to control their devices. Conventional systems enable such communications by performing overt actions that in some cases cannot otherwise be performed. For example, if a user is composing a verbal message in a public environment, the user's speech can be heard by others, which invades the user's privacy. Such a user may avoid composing the message until a later time, which can be burdensome. Also, many speech-to-text systems that operate using the voice of the user are still inaccurate and erroneously generate messages based on a user's speech. The users in such systems still need to manually perform corrections, which results in inefficient use of resources or lack of use.

Certain systems use EMG electrodes to detect silent speech of users. The silent speech can then be used in these systems to perform various operations. The success of these systems in detecting the silent speech heavily relies upon the accuracy of the EMG signals collected by the EMG electrodes, the accuracy at which users are able to produce the EMG signals, and the accuracy at which machine learning models can generate predictions of the intended phonemes, phoneme sounds, words or phrases associated with the inner speech being produced. In general, there exists an insufficient amount of available training data for training users and machine learning models to produce and classify inner speech. This is so because not only is there no "correct" form of producing inner speech, but the fact that it does not produce any sound makes it hard for the user to know whether they were doing it correctly or how to improve its production. The lack of sufficient training data makes it incredibly challenging to teach users how to accurately produce inner speech in a way that a machine learning model can accurately predict corresponding words. This reduces the accuracy of inner speech detection systems, which wastes resources and can end up frustrating end users.

A major hurdle in measuring human inner speech production quality is that learning may be needed before a person is able to produce inner speech in a way that would, on the one hand, be invisible, and on the other hand, create a robust and reproducible muscle activation pattern that can be detected and measured using an EMG device. While the premise of internal speech is that a person may engage in inner speech production without anyone else being aware of it, producing the 'right' kind of inner speech involves engaging in robust and consistent sub-threshold muscle activation, which may require some training.

According to the disclosed techniques, a system for synthetically generating inner speech training data from EMG data associated with overt speech is provided. The training data can then be used to train a machine learning model to accurately predict phonemes, phoneme sounds, words or phrases corresponding to EMG data associated with inner speech. In order to synthetically generate the inner speech training data, a relationship between a set of overt speech-based EMG data, inner speech-based EMG data, and resting based EMG data (where no speech is being performed) is established. This relationship is used to generate and compute a set of transformation parameters, such as a scaling parameter, a colored noise parameter, and a time shift parameter. These transformation parameters are then used to modify EMG data associated with overt speech to generate the inner speech training data.

The disclosed techniques access a collection of overt speech signals representing phonemes, phoneme sounds, words or phrases spoken at least partially using overt speech. The disclosed techniques transform the collection of overt speech signals into inner speech training data that includes EMG data representing inner speech corresponding to the phonemes, phoneme sounds, words or phrases spoken at least partially using the overt speech. The disclosed techniques train a machine learning model to decode inner speech signals into a set of corresponding phonemes, phoneme sounds, words or phrases based on the inner speech training data.

In some examples, the disclosed examples include an EMG communication device that includes a wearable collar, earphones, communication device, and a processing device. The EMG communication device can be in communication with a mobile device, an XR device, such as an AR headset, a VR headset, and/or with headphones, earbuds, or speakers. Any reference to AR operations and/or AR device below can be applied in a similar manner to an XR operation and/or XR device.

The disclosed techniques simplify the process of interacting with various applications and/or XR glasses or other wearable devices. The disclosed techniques enable seamless and efficient operation of XR experiences. The disclosed techniques improve the overall experience of the user in using the electronic device. After training the user and the ML model, the disclosed techniques allow a user to interact with features of an interaction application without performing any overt physical movement. Namely, a user can capture a screenshot, image, and/or video by performing inner speech and without moving any muscles associated with speech production or typing. In this way, the disclosed techniques reduce the number of resources needed to operate a given device and improve the overall efficiency of electronic devices. Additionally, the disclosed techniques increase the efficiency, appeal, and utility of electronic devices. The disclosed examples increase the efficiencies of the electronic device by reducing the number of pages of information and inputs needed to accomplish a task.

Networked Computing Environment

FIG. 1 is a block diagram showing an example interaction system 100 for facilitating interactions (e.g., exchanging text messages, conducting text audio and video calls, or playing games) over a network. The interaction system 100 includes multiple user systems 102, each of which hosts multiple applications, including an interaction client 104 and other applications 106. Each interaction client 104 is communicatively coupled, via one or more communication networks including a network 108 (e.g., the Internet), to other instances of the interaction client 104 (e.g., hosted on respective other user systems 102), an interaction server system 110 and third-party servers 112). An interaction client 104 can also communicate with locally hosted applications 106 using Applications Program Interfaces (APIs).

Each user system 102 may include multiple user devices, such as a mobile device 114, head-wearable apparatus 116, and a computer client device 118 that are communicatively connected to exchange data and messages.

An interaction client 104 interacts with other interaction clients 104 and with the interaction server system 110 via the network 108. The data exchanged between the interaction clients 104 (e.g., interactions 120) and between the interaction clients 104 and the interaction server system 110 includes functions (e.g., commands to invoke functions) and payload data (e.g., text, audio, video, or other multimedia data).

The interaction server system 110 provides server-side functionality via the network 108 to the interaction clients 104. While certain functions of the interaction system 100 are described herein as being performed by either an interaction client 104 or by the interaction server system 110, the location of certain functionality either within the interaction client 104 or the interaction server system 110 may be a design choice. For example, it may be technically preferable to initially deploy particular technology and functionality within the interaction server system 110 but to later migrate this technology and functionality to the interaction client 104 where a user system 102 has sufficient processing capacity.

The interaction server system 110 supports various services and operations that are provided to the interaction clients 104. Such operations include transmitting data to, receiving data from, and processing data generated by the interaction clients 104. This data may include message content, client device information, geolocation information, media augmentation and overlays, message content persistence conditions, entity relationship information, and live event information. Data exchanges within the interaction system 100 are invoked and controlled through functions available via user interfaces (UIs) of the interaction clients 104.

Turning now specifically to the interaction server system 110, an API server 122 is coupled to and provides programmatic interfaces to interaction servers 124, making the functions of the interaction servers 124 accessible to interaction clients 104, other applications 106 and third-party server 112. The interaction servers 124 are communicatively coupled to a database server 126, facilitating access to a database 128 that stores data associated with interactions processed by the interaction servers 124. Similarly, a web server 130 is coupled to the interaction servers 124 and provides web-based interfaces to the interaction servers 124. To this end, the web server 130 processes incoming network requests over the Hypertext Transfer Protocol (HTTP) and several other related protocols.

The API server 122 receives and transmits interaction data (e.g., commands and message payloads) between the interaction servers 124 and the user systems 102 (and, for example, interaction clients 104 and other application 106) and the third-party server 112. Specifically, the API server 122 provides a set of interfaces (e.g., routines and protocols) that can be called or queried by the interaction client 104 and other applications 106 to invoke functionality of the interaction servers 124. The API server 122 exposes various functions supported by the interaction servers 124, including account registration; login functionality; the sending of interaction data, via the interaction servers 124, from a particular interaction client 104 to another interaction client 104; the communication of media files (e.g., images or video) from an interaction client 104 to the interaction servers 124; the settings of a collection of media data (e.g., a story); the retrieval of a list of friends of a user of a user system 102; the retrieval of messages and content; the addition and deletion of entities (e.g., friends) to an entity relationship graph (e.g., the entity graph 310); the location of friends within an entity relationship graph; and opening an application event (e.g., relating to the interaction client 104).

The interaction servers 124 host multiple systems and subsystems, described below with reference to FIG. 2.

Linked Applications

Returning to the interaction client 104, features and functions of an external resource (e.g., a linked application 106 or applet) are made available to a user via an interface of the interaction client 104. In this context, "external" refers to the fact that the application 106 or applet is external to the interaction client 104. The external resource is often provided by a third party but may also be provided by the creator or provider of the interaction client 104. The interaction client 104 receives a user selection of an option to launch or access features of such an external resource. The external resource may be the application 106 installed on the user system 102 (e.g., a "native app"), or a small-scale version of the application (e.g., an "applet") that is hosted on the user system 102 or remote of the user system 102 (e.g., on third-party servers 112). The small-scale version of the application includes a subset of features and functions of the application (e.g., the full-scale, native version of the application) and is implemented using a markup-language document. In some examples, the small-scale version of the application (e.g., an "applet") is a web-based, markup-language version of the application and is embedded in the interaction client 104. In addition to using markup-language documents (e.g., a .*ml file), an applet may incorporate a scripting language (e.g., a .*js file or a .json file) and a style sheet (e.g., a .*ss file).

In response to receiving a user selection of the option to launch or access features of the external resource, the interaction client 104 determines whether the selected external resource is a web-based external resource or a locally-installed application 106. In some cases, applications 106 that are locally installed on the user system 102 can be launched independently of and separately from the interaction client 104, such as by selecting an icon corresponding to the application 106 on a home screen of the user system 102. Small-scale versions of such applications can be launched or accessed via the interaction client 104 and, in some examples, no or limited portions of the small-scale application can be accessed outside of the interaction client 104. The small-scale application can be launched by the interaction client 104 receiving, from a third-party server 112 for example, a markup-language document associated with the small-scale application and processing such a document.

In response to determining that the external resource is a locally-installed application 106, the interaction client 104 instructs the user system 102 to launch the external resource by executing locally-stored code corresponding to the external resource. In response to determining that the external resource is a web-based resource, the interaction client 104 communicates with the third-party servers 112 (for example) to obtain a markup-language document corresponding to the selected external resource. The interaction client 104 then processes the obtained markup-language document to present the web-based external resource within a user interface of the interaction client 104.

The interaction client 104 can notify a user of the user system 102, or other users related to such a user (e.g., "friends"), of activity taking place in one or more external resources. For example, the interaction client 104 can provide participants in a conversation (e.g., a chat session) in the interaction client 104 with notifications relating to the current or recent use of an external resource by one or more members of a group of users. One or more users can be invited to join in an active external resource or to launch a recently used but currently inactive (in the group of friends) external resource. The external resource can provide participants in a conversation, each using respective interaction clients 104, with the ability to share an item, status, state, or location in an external resource in a chat session with one or more members of a group of users. The shared item may be an interactive chat card with which members of the chat can interact, for example, to launch the corresponding external resource, view specific information within the external resource, or take the member of the chat to a specific location or state within the external resource. Within a given external resource, response messages can be sent to users on the interaction client 104. The external resource can selectively include different media items in the responses, based on a current context of the external resource.

The interaction client 104 can present a list of the available external resources (e.g., applications 106 or applets) to a user to launch or access a given external resource. This list can be presented in a context-sensitive menu. For example, the icons representing different ones of the application 106 (or applets) can vary based on how the menu is launched by the user (e.g., from a conversation interface or from a non-conversation interface).

Figure 6:
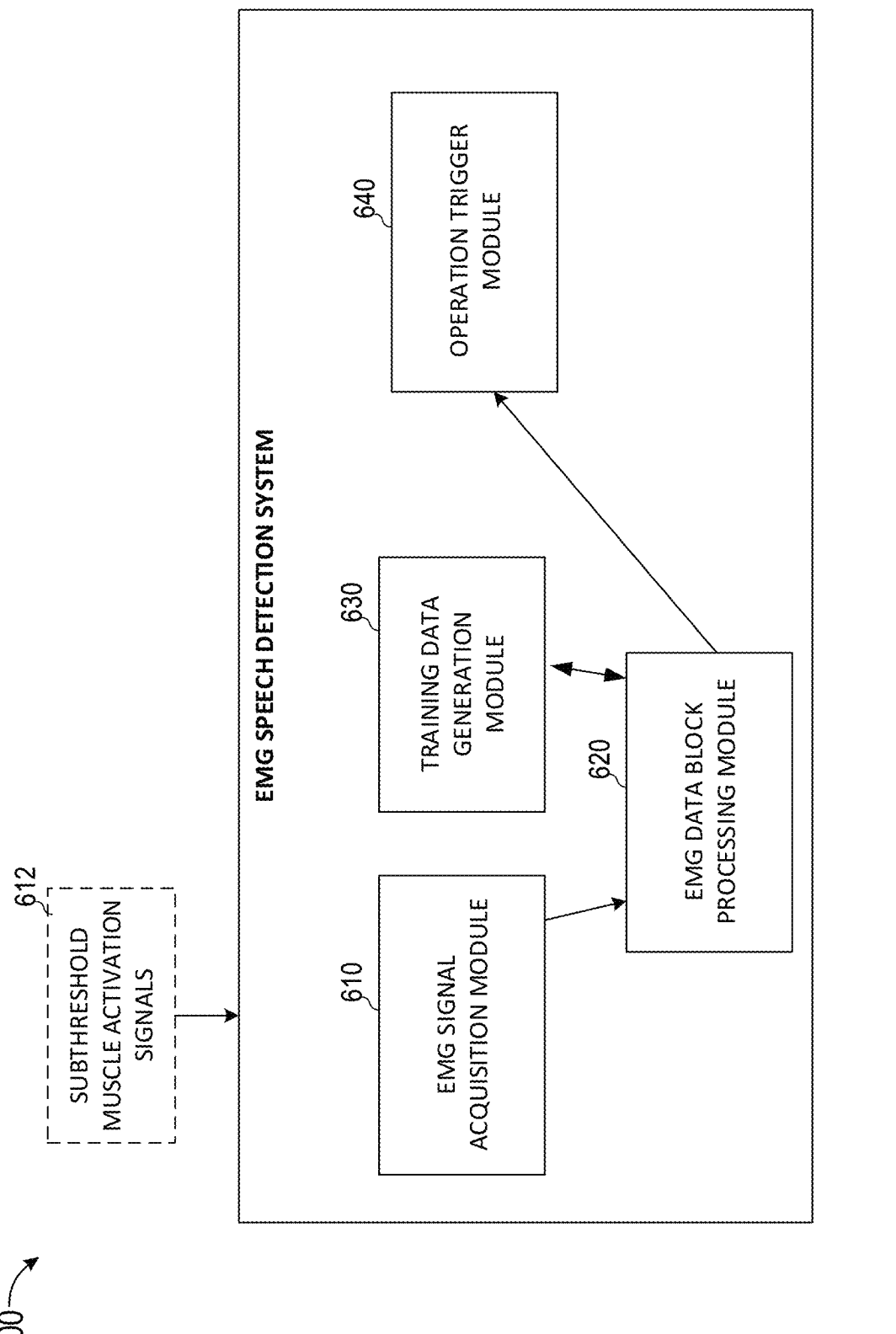
FIG. 6 is a diagrammatic representation of an EMG speech detection system, in accordance with some examples.

In some examples, the interaction client 104 utilizes an EMG speech detection system 600 of FIG. 6 to generate an AR experience in which one or more AR graphic elements are overlaid over a person depicted in an image or video. In some examples, the interaction client 104 utilizes the EMG speech detection system 600 to trigger various types of operations and/or actions or combinations of operations and/or actions. In some examples, the interaction client 104 utilizes the EMG speech detection system 600 to present an instruction to a user to produce inner and overt speech and collect EMG data corresponding to the inner and overt speech. The interaction client 104 utilizes the EMG speech detection system 600 to establish a relationship between the inner and overt speech EMG data along with rest-based EMG data to compute transformation parameters. The interaction client 104 then obtains a collection of overt speech EMG data to generate synthetic inner speech EMG data using the transformation parameters which is then used to train one or more ML models implemented by the EMG speech detection system 600. The interaction client 104 can utilize the EMG speech detection system 600 to process the EMG data by a machine learning model to generate a prediction comprising a word or phrase corresponding to the inner speech. Further details of the EMG speech detection system 600 are discussed below in connection with FIG. 6.

System Architecture

FIG. 2 is a block diagram illustrating further details regarding the interaction system 100, according to some examples. Specifically, the interaction system 100 is shown to comprise the interaction client 104 and the interaction servers 124. The interaction system 100 embodies multiple subsystems, which are supported on the client-side by the interaction client 104 and on the server-side by the interaction servers 124. Example subsystems are discussed below and can include an EMG speech detection system 600 that enables a user to control an interaction client/application/AR experience. An illustrative implementation of the EMG speech detection system 600 is shown and described in connection with FIG. 6 below.

In some examples, these subsystems are implemented as microservices. A microservice subsystem (e.g., a microservice application) may have components that enable it to operate independently and communicate with other services. Example components of a microservice subsystem may include:

Function logic: The function logic implements the functionality of the microservice subsystem, representing a specific capability or function that the microservice provides.

API interface: Microservices may communicate with other components through well-defined APIs or interfaces, using lightweight protocols such as REST or messaging. The API interface defines the inputs and outputs of the microservice subsystem and how it interacts with other microservice subsystems of the interaction system 100.

Data storage: A microservice subsystem may be responsible for its own data storage, which may be in the form of a database, cache, or other storage mechanism (e.g., using the database server 126 and database 128). This enables a microservice subsystem to operate independently of other microservices of the interaction system 100.

Service discovery: Microservice subsystems may find and communicate with other microservice subsystems of the interaction system 100. Service discovery mechanisms enable microservice subsystems to locate and communicate with other microservice subsystems in a scalable and efficient way.

Monitoring and logging: Microservice subsystems may need to be monitored and logged in order to ensure availability and performance. Monitoring and logging mechanisms enable the tracking of health and performance of a microservice subsystem.

In some examples, the interaction system 100 may employ a monolithic architecture, a service-oriented architecture (SOA), a function-as-a-service (FaaS) architecture, or a modular architecture:

An image processing system 202 provides various functions that enable a user to capture and augment (e.g., annotate or otherwise modify or edit) media content associated with a message.

A camera system 204 includes control software (e.g., in a camera application) that interacts with and controls camera hardware (e.g., directly or via operating system controls) of the user system 102 to modify and augment real-time images captured and displayed via the interaction client 104.

The augmentation system 206 provides functions related to the generation and publishing of augmentations (e.g., media overlays) for images captured in real-time by cameras of the user system 102 or retrieved from memory of the user system 102. For example, the augmentation system 206 operatively selects, presents, and displays media overlays (e.g., an image filter or an image lens) to the interaction client 104 for the augmentation of real-time images received via the camera system 204 or stored images retrieved from memory 1102 (shown in FIG. 11) of a user system 102. These augmentations are selected by the augmentation system 206 and presented to a user of an interaction client 104, based on a number of inputs and data, such as for example:

Geolocation of the user system 102; and

Entity relationship information of the user of the user system 102.

An augmentation may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo or video) at user system 102 for communication in a message, or applied to video content, such as a video content stream or feed transmitted from an interaction client 104. As such, image processing system 202 may interact with, and support, the various subsystems of the communication system 208, such as the messaging system 210 and the video communication system 212.

A media overlay may include text or image data that can be overlaid on top of a photograph taken by the user system 102 or a video stream produced by the user system 102. In some examples, the media overlay may be a location overlay (e.g., Venice beach), a name of a live event, or a name of a merchant overlay (e.g., Beach Coffee House). In further examples, the image processing system 202 uses the geolocation of the user system 102 to identify a media overlay that includes the name of a merchant at the geolocation of the user system 102. The media overlay may include other indicia associated with the merchant. The media overlays may be stored in the databases 128 and accessed through the database server 126.

The image processing system 202 provides a user-based publication platform that enables users to select a geolocation on a map and upload content associated with the selected geolocation. The user may also specify circumstances under which a particular media overlay should be offered to other users. The image processing system 202 generates a media overlay that includes the uploaded content and associates the uploaded content with the selected geolocation.

The augmentation creation system 214 supports augmented reality developer platforms and includes an application for content creators (e.g., artists and developers) to create and publish augmentations (e.g., augmented reality experiences) of the interaction client 104. The augmentation creation system 214 provides a library of built-in features and tools to content creators including, for example, custom shaders, tracking technology, and templates.

In some examples, the augmentation creation system 214 provides a merchant-based publication platform that enables merchants to select a particular augmentation associated with a geolocation via a bidding process. For example, the augmentation creation system 214 associates a media overlay of the highest bidding merchant with a corresponding geolocation for a predefined amount of time.

A communication system 208 is responsible for enabling and processing multiple forms of communication and interaction within the interaction system 100 and includes a messaging system 210, an audio communication system 216, and a video communication system 212. The messaging system 210 is responsible for enforcing the temporary or time-limited access to content by the interaction clients 104. The messaging system 210 incorporates multiple timers (e.g., within a user management system 218) that, based on duration and display parameters associated with a message or collection of messages (e.g., a story), selectively enable access (e.g., for presentation and display) to messages and associated content via the interaction client 104. The audio communication system 216 enables and supports audio communications (e.g., real-time audio chat) between multiple interaction clients 104. Similarly, the video communication system 212 enables and supports video communications (e.g., real-time video chat) between multiple interaction clients 104.

A user management system 218 is operationally responsible for the management of user data and profiles, and maintains entity information (e.g., stored in entity tables 308, entity graphs 310, and profile data 302) regarding users and relationships between users of the interaction system 100.

A collection management system 220 is operationally responsible for managing sets or collections of media (e.g., collections of text, image video, and audio data). A collection of content (e.g., messages, including images, video, text, and audio) may be organized into an "event gallery" or an "event story." Such a collection may be made available for a specified time period, such as the duration of an event to which the content relates. For example, content relating to a music concert may be made available as a "story" for the duration of that music concert. The collection management system 220 may also be responsible for publishing an icon that provides notification of a particular collection to the user interface of the interaction client 104. The collection management system 220 includes a curation function that allows a collection manager to manage and curate a particular collection of content. For example, the curation interface enables an event organizer to curate a collection of content relating to a specific event (e.g., to delete inappropriate content or redundant messages). Additionally, the collection management system 220 employs machine vision (or image recognition technology) and content rules to curate a content collection automatically. In certain examples, compensation may be paid to a user to include user-generated content in a collection. In such cases, the collection management system 220 operates to automatically make payments to such users to use their content.

A map system 222 provides various geographic location (e.g., geolocation) functions and supports the presentation of map-based media content and messages by the interaction client 104. For example, the map system 222 enables the display of user icons or avatars (e.g., stored in profile data 302 of FIG. 3) on a map to indicate a current or past location of "friends" of a user, as well as media content (e.g., collections of messages including photographs and videos) generated by such friends, within the context of a map. For example, a message posted by a user to the interaction system 100 from a specific geographic location may be displayed within the context of a map at that particular location to "friends" of a specific user on a map interface of the interaction client 104. A user can furthermore share his or her location and status information (e.g., using an appropriate status avatar) with other users of the interaction system 100 via the interaction client 104, with this location and status information being similarly displayed within the context of a map interface of the interaction client 104 to selected users.

A game system 224 provides various gaming functions within the context of the interaction client 104. The interaction client 104 provides a game interface providing a list of available games that can be launched by a user within the context of the interaction client 104 and played with other users of the interaction system 100. The interaction system 100 further enables a particular user to invite other users to participate in the play of a specific game by issuing invitations to such other users from the interaction client 104. The interaction client 104 also supports audio, video, and text messaging (e.g., chats) within the context of gameplay, provides a leaderboard for the games, and also supports the provision of in-game rewards (e.g., coins and items).

An external resource system 226 provides an interface for the interaction client 104 to communicate with remote servers (e.g., third-party servers 112) to launch or access external resources, i.e., applications or applets. Each third-party server 112 hosts, for example, a markup language (e.g., HTML5) based application or a small-scale version of an application (e.g., game, utility, payment, or ride-sharing application). The interaction client 104 may launch a web-based resource (e.g., application) by accessing the HTML5 file from the third-party servers 112 associated with the web-based resource. Applications hosted by third-party servers 112 are programmed in JavaScript leveraging a Software Development Kit (SDK) provided by the interaction servers 124. The SDK includes Application Programming Interfaces (APIs) with functions that can be called or invoked by the web-based application. The interaction servers 124 host a JavaScript library that provides a given external resource access to specific user data of the interaction client 104. HTML5 is an example of technology for programming games, but applications and resources programmed based on other technologies can be used.

To integrate the functions of the SDK into the web-based resource, the SDK is downloaded by the third-party server 112 from the interaction servers 124 or is otherwise received by the third-party server 112. Once downloaded or received, the SDK is included as part of the application code of a web-based external resource. The code of the web-based resource can then call or invoke certain functions of the SDK to integrate features of the interaction client 104 into the web-based resource.

The SDK stored on the interaction server system 110 effectively provides the bridge between an external resource (e.g., applications 106 or applets) and the interaction client 104. This gives the user a seamless experience of communicating with other users on the interaction client 104 while also preserving the look and feel of the interaction client 104. To bridge communications between an external resource and an interaction client 104, the SDK facilitates communication between third-party servers 112 and the interaction client 104. A bridge script running on a user system 102 establishes two one-way communication channels between an external resource and the interaction client 104. Messages are sent between the external resource and the interaction client 104 via these communication channels asynchronously. Each SDK function invocation is sent as a message and callback. Each SDK function is implemented by constructing a unique callback identifier and sending a message with that callback identifier.

By using the SDK, not all information from the interaction client 104 is shared with third-party servers 112. The SDK limits which information is shared based on the needs of the external resource. Each third-party server 112 provides an HTML5 file corresponding to the web-based external resource to interaction servers 124. The interaction servers 124 can add a visual representation (such as a box art or other graphic) of the web-based external resource in the interaction client 104. Once the user selects the visual representation or instructs the interaction client 104 through a graphical user interface (GUI) of the interaction client 104 to access features of the web-based external resource, the interaction client 104 obtains the HTML5 file and instantiates the resources to access the features of the web-based external resource.

The interaction client 104 presents a graphical user interface (e.g., a landing page or title screen) for an external resource. During, before, or after presenting the landing page or title screen, the interaction client 104 determines whether the launched external resource has been previously authorized to access user data of the interaction client 104. In response to determining that the launched external resource has been previously authorized to access user data of the interaction client 104, the interaction client 104 presents another graphical user interface of the external resource that includes functions and features of the external resource. In response to determining that the launched external resource has not been previously authorized to access user data of the interaction client 104, after a threshold period of time (e.g., 3 seconds) of displaying the landing page or title screen of the external resource, the interaction client 104 slides up (e.g., animates a menu as surfacing from a bottom of the screen to a middle or other portion of the screen) a menu for authorizing the external resource to access the user data. The menu identifies the type of user data that the external resource will be authorized to use. In response to receiving a user selection of an accept option, the interaction client 104 adds the external resource to a list of authorized external resources and allows the external resource to access user data from the interaction client 104. The external resource is authorized by the interaction client 104 to access the user data under an OAuth 2 framework.

The interaction client 104 controls the type of user data that is shared with external resources based on the type of external resource being authorized. For example, external resources that include full-scale applications (e.g., an application 106) are provided with access to a first type of user data (e.g., two-dimensional avatars of users with or without different avatar characteristics). As another example, external resources that include small-scale versions of applications (e.g., web-based versions of applications) are provided with access to a second type of user data (e.g., payment information, two-dimensional avatars of users, three-dimensional avatars of users, and avatars with various avatar characteristics). Avatar characteristics include different ways to customize a look and feel of an avatar, such as different poses, facial features, clothing, and so forth.

An advertisement system 228 operationally enables the purchasing of advertisements by third parties for presentation to end-users via the interaction clients 104 and also handles the delivery and presentation of these advertisements.

An artificial intelligence and machine learning system 230 provides a variety of services to different subsystems within the interaction system 100. For example, the artificial intelligence and machine learning system 230 operates with the image processing system 202 and the camera system 204 to analyze images and extract information such as objects, text, or faces. This information can then be used by the image processing system 202 to enhance, filter, or manipulate images. The artificial intelligence and machine learning system 230 may be used by the augmentation system 206 to generate augmented content and augmented reality experiences, such as adding virtual objects or animations to real-world images.

The communication system 208 and messaging system 210 may use the artificial intelligence and machine learning system 230 to analyze communication patterns and provide insights into how users interact with each other and provide intelligent message classification and tagging, such as categorizing messages based on sentiment or topic. The artificial intelligence and machine learning system 230 may also provide chatbot functionality to message interactions 120 between user systems 102 and between a user system 102 and the interaction server system 110. The artificial intelligence and machine learning system 230 may also work with the audio communication system 216 to provide speech recognition and natural language processing capabilities, allowing users to interact with the interaction system 100 using voice commands.

The artificial intelligence and machine learning system 230 can be implemented as part of the EMG speech detection system 600 and can be used to classify EMG signals to generate predictions of one or more phonemes, phoneme sounds, words or phrases corresponding to inner speech used to produce the EMG signals. These predictions can be evaluated together with evaluations of how well a user produced the inner speech to train a user and the artificial intelligence and machine learning system 230 together. Once trained, the artificial intelligence and machine learning system 230 can be used in real time to classify EMG signals to generate predictions and use such predictions to perform various operations and actions of the interaction client 104 and/or user system 102.

Data Architecture

Figure 3:
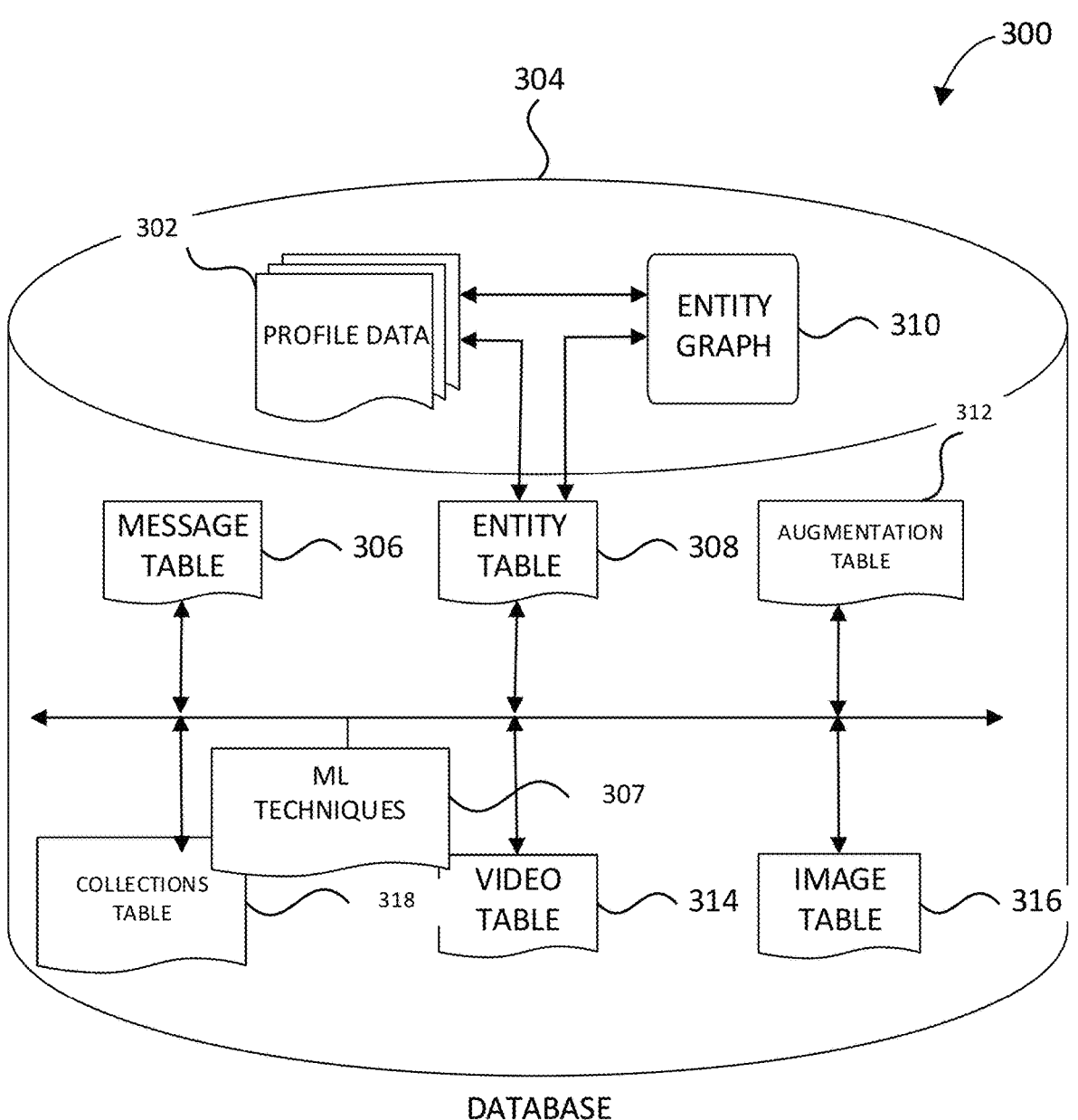
FIG. 3 is a diagrammatic representation of a data structure as maintained in a database, according to some examples.

FIG. 3 is a schematic diagram illustrating data structures 300, which may be stored in the database 304 of the interaction server system 110, according to certain examples. While the content of the database 304 is shown to comprise multiple tables, it will be appreciated that the data could be stored in other types of data structures (e.g., as an object-oriented database).

The database 304 includes message data stored within a message table 306. This message data includes, for any particular message, at least message sender data, message recipient (or receiver) data, and a payload. Further details regarding information that may be included in a message and included within the message data stored in the message table 306, are described below with reference to FIG. 4.

An entity table 308 stores entity data and is linked (e.g., referentially) to an entity graph 310 and profile data 302. Entities for which records are maintained within the entity table 308 may include individuals, corporate entities, organizations, objects, places, events, and so forth. Regardless of entity type, any entity regarding which the interaction server system 110 stores data may be a recognized entity. Each entity is provided with a unique identifier, as well as an entity type identifier (not shown).

The entity graph 310 stores information regarding relationships and associations between entities. Such relationships may be social, professional (e.g., work at a common corporation or organization), interest-based, or activity-based, merely for example. Certain relationships between entities may be unidirectional, such as a subscription by an individual user to digital content of a commercial or publishing user (e.g., a newspaper or other digital media outlet, or a brand). Other relationships may be bidirectional, such as a "friend" relationship between individual users of the interaction system 100.

Certain permissions and relationships may be attached to each relationship, and also to each direction of a relationship. For example, a bidirectional relationship (e.g., a friend relationship between individual users) may include authorization for the publication of digital content items between the individual users but may impose certain restrictions or filters on the publication of such digital content items (e.g., based on content characteristics, location data or time of day data). Similarly, a subscription relationship between an individual user and a commercial user may impose different degrees of restrictions on the publication of digital content from the commercial user to the individual user and may significantly restrict or block the publication of digital content from the individual user to the commercial user. A particular user, as an example of an entity, may record certain restrictions (e.g., by way of privacy settings) in a record for that entity within the entity table 308. Such privacy settings may be applied to all types of relationships within the context of the interaction system 100 or may selectively be applied to certain types of relationships.

The profile data 302 stores multiple types of profile data about a particular entity. The profile data 302 may be selectively used and presented to other users of the interaction system 100 based on privacy settings specified by a particular entity. Where the entity is an individual, the profile data 302 includes, for example, a username, telephone number, address, settings (e.g., notification and privacy settings), as well as a user-selected avatar representation (or collection of such avatar representations). A particular user may then selectively include one or more of these avatar representations within the content of messages communicated via the interaction system 100, and on map interfaces displayed by interaction clients 104 to other users. The collection of avatar representations may include "status avatars," which present a graphical representation of a status or activity that the user may select to communicate at a particular time.

Where the entity is a group, the profile data 302 for the group may similarly include one or more avatar representations associated with the group, in addition to the group name, members, and various settings (e.g., notifications) for the relevant group.

The database 304 also stores augmentation data, such as overlays or filters, in an augmentation table 312. The augmentation data is associated with and applied to videos (for which data is stored in a video table 314) and images (for which data is stored in an image table 316).

Filters, in some examples, are overlays that are displayed as overlaid on an image or video during presentation to a recipient user. Filters may be of various types, including user-selected filters from a set of filters presented to a sending user by the interaction client 104 when the sending user is composing a message. Other types of filters include geolocation filters (also known as geo-filters), which may be presented to a sending user based on geographic location. For example, geolocation filters specific to a neighborhood or special location may be presented within a user interface by the interaction client 104, based on geolocation information determined by a Global Positioning System (GPS) unit of the user system 102.

Another type of filter is a data filter, which may be selectively presented to a sending user by the interaction client 104 based on other inputs or information gathered by the user system 102 during the message creation process. Examples of data filters include current temperature at a specific location, a current speed at which a sending user is traveling, battery life for a user system 102, or the current time.

Other augmentation data that may be stored within the image table 316 includes augmented reality content items (e.g., corresponding to applying "lenses" or augmented reality experiences). An augmented reality content item may be a real-time special effect and sound that may be added to an image or a video.

A collections table 318 stores data regarding collections of messages and associated images, videos, or audio data, which are compiled into a collection (e.g., a story or a gallery). The creation of a particular collection may be initiated by a particular user (e.g., each user for which a record is maintained in the entity table 308). A user may create a "personal story" in the form of a collection of content that has been created and sent/broadcast by that user. To this end, the user interface of the interaction client 104 may include an icon that is user-selectable to enable a sending user to add specific content to his or her personal story.

A collection may also constitute a "live story," which is a collection of content from multiple users that is created manually, automatically, or using a combination of manual and automatic techniques. For example, a "live story" may constitute a curated stream of user-submitted content from various locations and events. Users whose client devices have location services enabled and are at a common location event at a particular time may, for example, be presented with an option, via a user interface of the interaction client 104, to contribute content to a particular live story. The live story may be identified to the user by the interaction client 104, based on his or her location. The end result is a "live story" told from a community perspective.

A further type of content collection is known as a "location story," which enables a user whose user system 102 is located within a specific geographic location (e.g., on a college or university campus) to contribute to a particular collection. In some examples, a contribution to a location story may employ a second degree of authentication to verify that the end-user belongs to a specific organization or other entity (e.g., is a student on the university campus).

As mentioned above, the video table 314 stores video data that, in some examples, is associated with messages for which records are maintained within the message table 306. Similarly, the image table 316 stores image data associated with messages for which message data is stored in the entity table 308. The entity table 308 may associate various augmentations from the augmentation table 312 with various images and videos stored in the image table 316 and the video table 314.

The databases 304 also include trained machine learning (ML) technique(s) 307 that stores parameters of one or more machine learning models that have been trained during training of the EMG speech detection system 600. For example, trained machine learning techniques 307 stores the trained parameters of one or more artificial neural network machine learning models or techniques.

Data Communications Architecture

Figure 4:
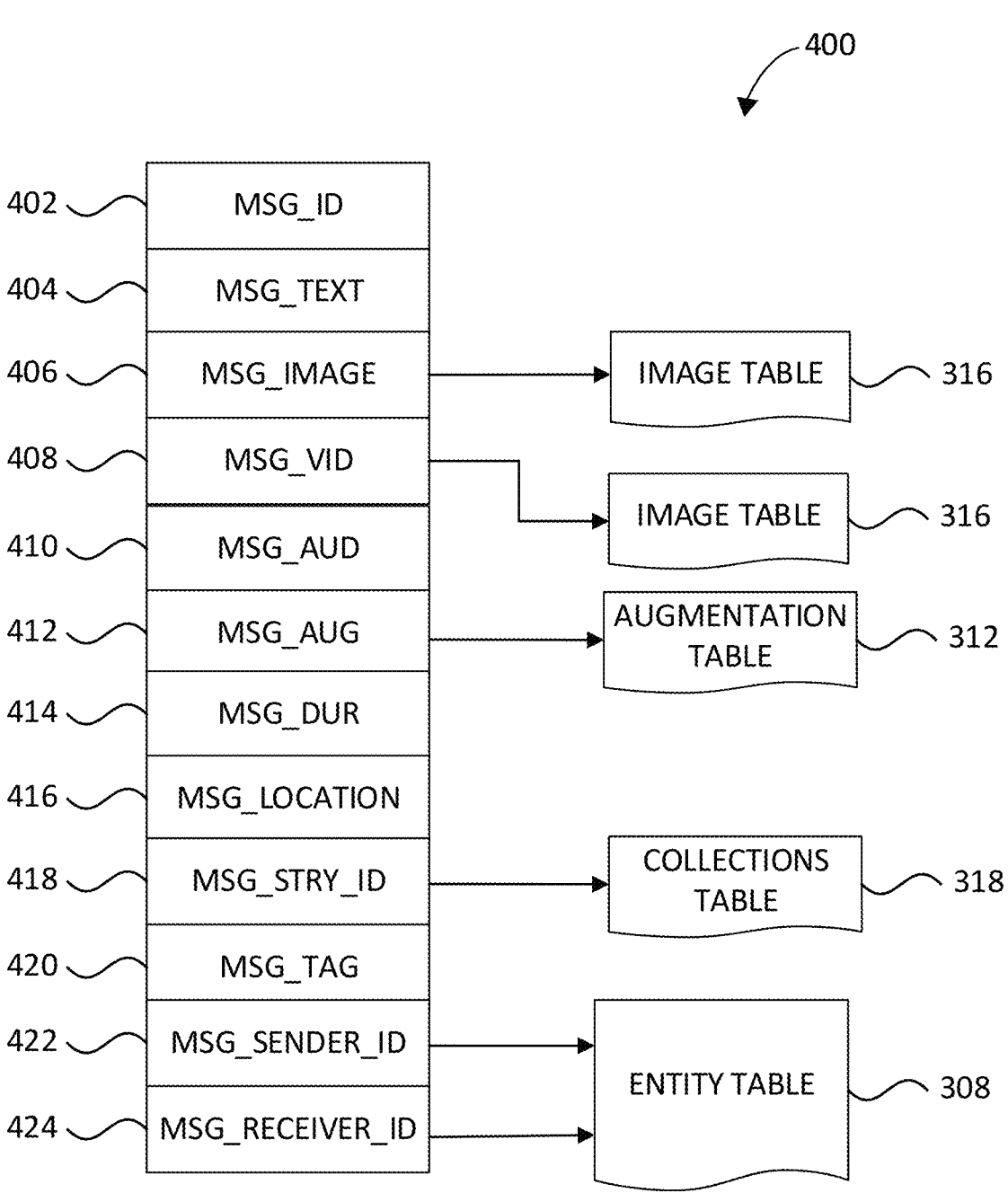
FIG. 4 is a diagrammatic representation of a message, according to some examples.

FIG. 4 is a schematic diagram illustrating a structure of a message 400, according to some examples, generated by an interaction client 104 for communication to a further inter-action client 104 via the interaction servers 124. The content of a particular message 400 is used to populate the message table 306 stored within the database 304, accessible by the interaction servers 124. Similarly, the content of a message 400 is stored in memory as "in-transit" or "in-flight" data of the user system 102 or the interaction servers 124. A message 400 is shown to include the following example components:

Message identifier 402: a unique identifier that identifies the message 400.

Message text payload 404: text, to be generated by a user via a user interface of the user system 102, and that is included in the message 400.

Message image payload 406: image data, captured by a camera component of a user system 102 or retrieved from a memory component of a user system 102, and that is included in the message 400. Image data for a sent or received message 400 may be stored in the image table 316.

Message video payload 408: video data, captured by a camera component or retrieved from a memory com-ponent of the user system 102, and that is included in the message 400. Video data for a sent or received message 400 may be stored in the image table 316.

Message audio payload 410: audio data, captured by a microphone or retrieved from a memory component of the user system 102, and that is included in the message 400.

Message augmentation data 412: augmentation data (e.g., filters, stickers, or other annotations or enhancements) that represents augmentations to be applied to message image payload 406, message video payload 408, or message audio payload 410 of the message 400. Aug-mentation data for a sent or received message 400 may be stored in the augmentation table 312.

Message duration parameter 414: parameter value indi-cating, in seconds, the amount of time for which content of the message (e.g., the message image pay-load 406, message video payload 408, message audio payload 410) is to be presented or made accessible to a user via the interaction client 104.

Message geolocation parameter 416: geolocation data (e.g., latitudinal and longitudinal coordinates) associ-ated with the content payload of the message. Multiple message geolocation parameter 416 values may be included in the payload, each of these parameter values being associated with respect to content items included in the content (e.g., a specific image within the message image payload 406, or a specific video in the message video payload 408).

Message story identifier 418: identifier values identifying one or more content collections (e.g., "stories" identified in the collections table 318) with which a particular content item in the message image payload 406 of the message 400 is associated. For example, multiple images within the message image payload 406 may each be associated with multiple content collections using identifier values.

Message tag 420: each message 400 may be tagged with multiple tags, each of which is indicative of the subject matter of content included in the message payload. For example, where a particular image included in the message image payload 406 depicts an animal (e.g., a lion), a tag value may be included within the message tag 420 that is indicative of the relevant animal. Tag values may be generated manually, based on user input, or may be automatically generated using, for example, image recognition.

Message sender identifier 422: an identifier (e.g., a mes-saging system identifier, email address, or device iden-tifier) indicative of a user of the user system 102 on which the message 400 was generated and from which the message 400 was sent.

Message receiver identifier 424: an identifier (e.g., a messaging system identifier, email address, or device identifier) indicative of a user of the user system 102 to which the message 400 is addressed.

The contents (e.g., values) of the various components of message 400 may be pointers to locations in tables within which content data values are stored. For example, an image value in the message image payload 406 may be a pointer to (or address of) a location within an image table 316. Similarly, values within the message video payload 408 may point to data stored within an image table 316, values stored within the message augmentation data 412 may point to data stored in an augmentation table 312, values stored within the message story identifier 418 may point to data stored in a collections table 318, and values stored within the message sender identifier 422 and the message receiver identifier 424 may point to user records stored within an entity table 308.

EMG Communication Device

Figure 5:
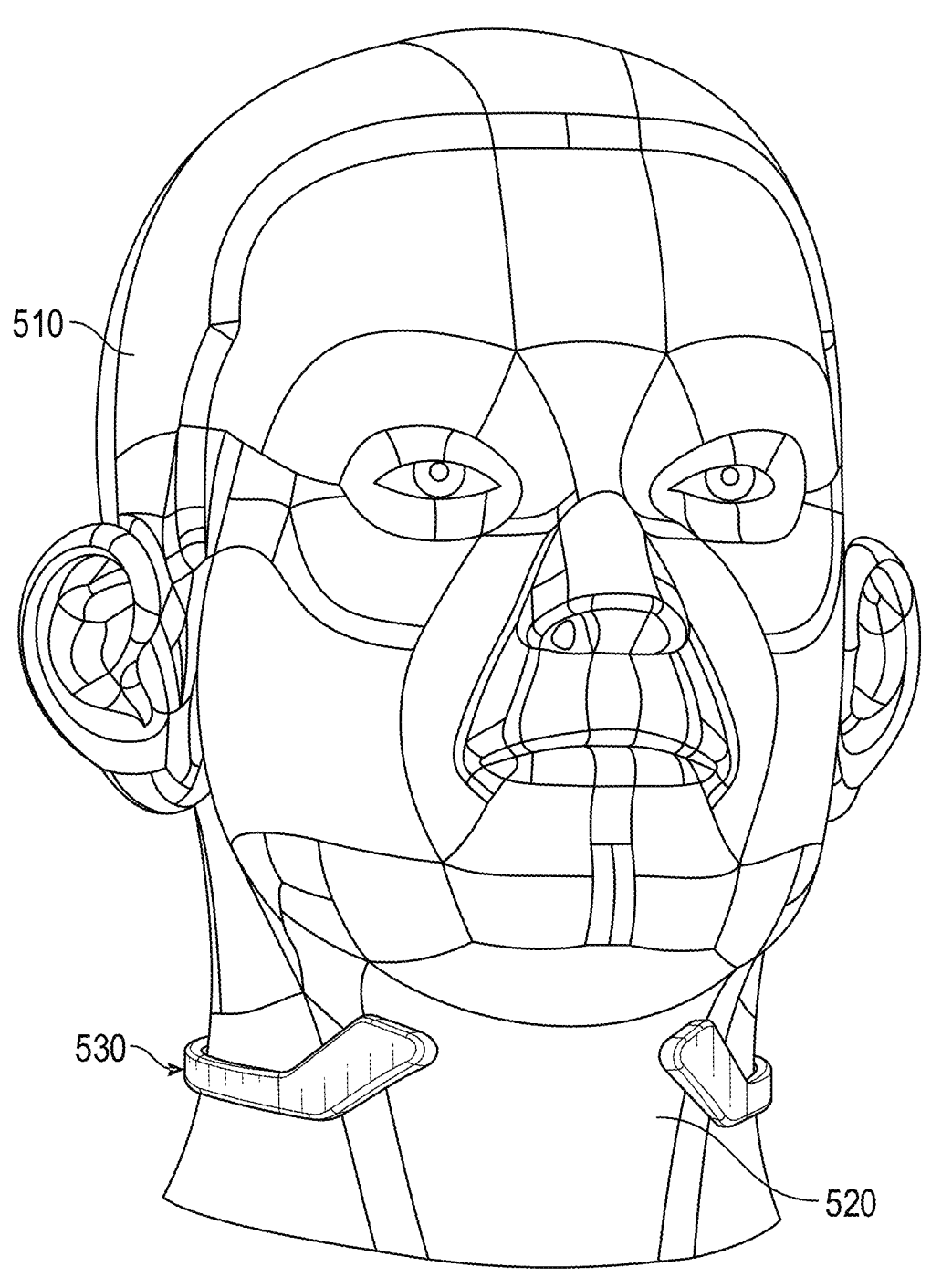
FIG. 5 is a diagrammatic representation of a user wearing an EMG communication device, in accordance with some examples.

FIG. 5 is a diagrammatic representation of a user 510 wearing the EMG communication device 530, in accordance with some examples. As shown, the EMG communication device 530 is placed behind a neck 520 of the user 510. The EMG communication device 530 can completely encircle the neck 520 or partially encircle the neck 520 of the user 510.

The EMG communication device 530 includes a body that can wrap around the back or front of a user's neck. The body includes an array of EMG electrodes on one or both ends of the EMG communication device 530. In this way, when the EMG communication device 530 is worn by a user 510, a first set of the array of EMG electrodes can capture or detect subthreshold muscle activation signals on a left side of the user's neck 520, and a second set of the array of EMG electrodes can capture or detect subthreshold muscle acti-vation signals on a right side of the user's neck 520. The body of the EMG communication device 530 can be made from any suitable material such as plastics or metal, includ-ing any suitable shape memory alloy. The body of the EMG communication device 530 can include a touch input inter-face that is configured to receive touch input from a user (e.g., one finger touch, two finger touch, or combination thereof together) to control operations of the EMG commu-nication device 530, such as to turn the EMG communica-tion device 530 ON/OFF, place the EMG communication device 530 into hibernation mode (in which the EMG electrodes are disabled or deactivated to save battery), place the EMG communication device 530 into an active mode (in which the EMG electrodes are enabled or activated to detect subthreshold muscle activation signals, and/or a capture mode in which the EMG communication device 530 starts recording the subthreshold muscle activation signals detected by the EMG electrodes).

The EMG communication device 530 has onboard electronics components including a computing device, such as a computer or low power processor, which can, in different examples, be of any suitable type so as to be carried by the body of the EMG communication device 530. In some examples, the computer is at least partially housed in one or both ends of the body of the EMG communication device 530. The computer includes one or more processors with memory (e.g., a volatile storage device, such as random access memory or registers) and a storage device (e.g., a non-volatile storage device), and can be in communication with a wireless communication circuitry (e.g., WiFi, Bluetooth low energy (BLE) communication devices and/or WiFi direct devices) and a power source. The computer can include low-power circuitry, high-speed circuitry, and, in some examples, a display processor. Various examples may include these elements in different configurations or integrated together in different ways.

The computer additionally includes a battery or other suitable portable power supply. In some examples, the battery is disposed in one of the ends of the body of the EMG communication device 530. The onboard computer and the EMG electrodes are configured together to provide at least a part of the EMG speech detection system 600 that automatically or selectively captures EMG subthreshold muscle activation signals and triggers actions/operations when inner speech represented by the EMG subthreshold muscle activation signals is collected over a continuous or non-continuous interval of time. In some examples, progress of the collection and detection of the inner speech is transmitted to AR glasses or user system 102 and/or to one or more headphones or earbuds worn by a user and/or to a remote server for further processing, such as to present a progress bar that is increased or decreased in size based on detection of existence or absence of inner speech.

The EMG communication device 530 can include an accelerometer and a touch interface and a voice command system. Based on input received by the EMG communication device 530 from the accelerometer and a touch interface, the EMG communication device 530 can improve calibration and placement of the EMG communication device 530 and the EMG electrodes. The EMG communication device 530 can include one or more communication device(s) to communicate with a user system 102 and/or a remote server. The EMG communication device 530 can communicate via the one or more communication device(s), to the user system 102 or the remote server, the raw EMG signals captured by the EMG electrodes and/or processed data and/or speech features estimated from the raw EMG signals captured by the EMG electrodes. The communication device of the EMG communication device 530 allows the EMG communication device 530 to connect to the user system 102 and/or to AR glasses over a secure or unsecure Bluetooth low-energy (BLE) connection.

The EMG communication device 530 includes a microphone (e.g., bone conductive microphone). The microphone can be used in one or more training modes of the EMG communication device 530 to capture spoken commands and compare such spoken commands to the speech features estimated from the associated EMG signals. The microphone of the EMG communication device 530 can also be used to monitor continuously for a trigger word. The trigger word can instruct the EMG communication device 530 to begin capturing and storing data from the EMG electrodes. Namely, the trigger word can be spoken by a user when the user intends to perform inner speech and use the inner speech to control one or more operations of the user system 102 (e.g., an interaction client 104). The captured and stored data from the EMG electrodes can then be processed by a trained machine learning technique to estimate one or more speech features, such as after filtering the data to remove interfering signals. The one or more speech features can then be further processed by one or more additional neural networks or machine learning techniques to generate an audible response or visual response.

The EMG communication device 530 can also include or be associated with one or more speakers (not shown). The one or more speakers can be used to audibly output the audible response estimated and generated from the subthreshold muscle activation signals detected and captured by the EMG electrodes. Based on the user hearing the audible response from the one or more speakers, the user can mentally adjust future inner speech generation to control the output of the EMG communication device 530 more accurately.

The one or more communication devices can include a BLE communication interface. Such BLE communication interface enables the EMG communication device 530 to communicate wirelessly with the user system 102. Other forms of wireless communication can also be employed instead of, or in addition to, the BLE communication interface, such as a WiFi direct interface. The BLE communication interface implements a standard number of BLE communication protocols.

A first of the communications protocols implemented by the BLE interface of the EMG communication device 530 enables an unencrypted link to be established between the EMG communication device 530 and the user system 102. In this first protocol, the link-layer communication (the physical interface or medium) between the EMG communication device 530 and the user system 102 includes unencrypted data. In this first protocol, the application layer (the communication layer operating on the physically exchanged data) encrypts and decrypts data that is physically exchanged in unencrypted form over the link layer of the BLE communication interface. In this way, data exchanged over the physical layer can be read freely by an eavesdropping device, but the eavesdropping device will not be able to decipher the data that is exchanged without performing a decryption operation in the application layer.

A second of the communications protocols implemented by the BLE interface of the EMG communication device 530 enables an encrypted link to be established between the EMG communication device 530 and the user system 102 and/or AR glasses. In this second protocol, the link-layer communication (the physical interface) between the EMG communication device 530 and the user system 102 receives data from the application layer and adds a first type of encryption to the data before exchanging the data over the physical medium. In this second protocol, the application layer (the communication layer operating on the physically exchanged data) may or may not use a second type of encryption to encrypt and decrypt data that is physically exchanged in encrypted form, using the first type of encryption, over the link layer of the BLE communication interface. Namely, data can be first encrypted by the application layer and then be further encrypted by the physical layer before being exchanged over the physical medium. Following the exchange over the physical medium, the data is then decrypted by the physical layer and then decrypted again (e.g., using a different type of encryption) by the application layer. In this way, data exchanged over the physical layer cannot be read by an eavesdropping device as the data is encrypted in the physical medium.

In some examples, the user system 102 communicates with the EMG communication device 530 using the first protocol to exchange raw EMG signals and uses the second protocol to exchange speech features estimated from the raw (or filtered) EMG signals (e.g., existence or absence of inner speech) between the interaction client 104 and the EMG communication device 530. In some examples, the EMG communication device 530 communicates with one or more servers to provide the raw EMG signals from the EMG communication device 530 to the one or more servers for processing and generating one or more EMG data blocks. Once processed by the one or more servers, the one or more EMG data blocks are returned to the EMG communication device 530 for further processing, training, and calibrating a threshold for STA detection based on visual and/or audible feedback presented to a user.

EMG Speech Detection System

FIG. 6 is a block diagram showing an example EMG speech detection system 600, according to some examples. The EMG speech detection system 600 receives subthreshold muscle activation signals 612 (STA signals) and includes an EMG signal acquisition module 610, an EMG data block processing module 620, a training data generation module 630, and an operation trigger module 640. In some cases, the EMG speech detection system 600 detects electrical activity in response to a nerve's stimulation of the muscle and transduces the physiological electrical response into auditory and/or visual stimuli for the user ("feedback"). The EMG speech detection system 600 detects electrical responses associated with actual muscle contractions, such as physical movement of facial muscles and neck clenching or movement, as well as electrical responses associated with imagined muscle contractions, such as inner speech in which a user imagines in their mind the performance of the act of speaking, which would normally be subliminal. Feedback can be provided in a continuous manner or periodic manner while the EMG speech detection system 600 monitors the electrical input. In some examples, a beep or other suitable sound is played and/or a visual indication appears every time the EMG speech detection system 600 detects an EMG signature compatible with actual or imagined contraction.

In some examples, the EMG speech detection system 600 detects presence of inner speech in EMG data. For example, the EMG speech detection system 600 applies a trained machine learning model to a set of EMG signals to estimate a probability that inner speech is present or is represented by the combination of EMG signals. In some cases, the EMG speech detection system 600 compares an attribute, such as a level of intensity and/or frequency, associated with one or more of the set of EMG signals to a minimum threshold and when that minimum threshold is transgressed, the EMG speech detection system 600 determines that inner speech is represented by the EMG signals.

Figure 7:
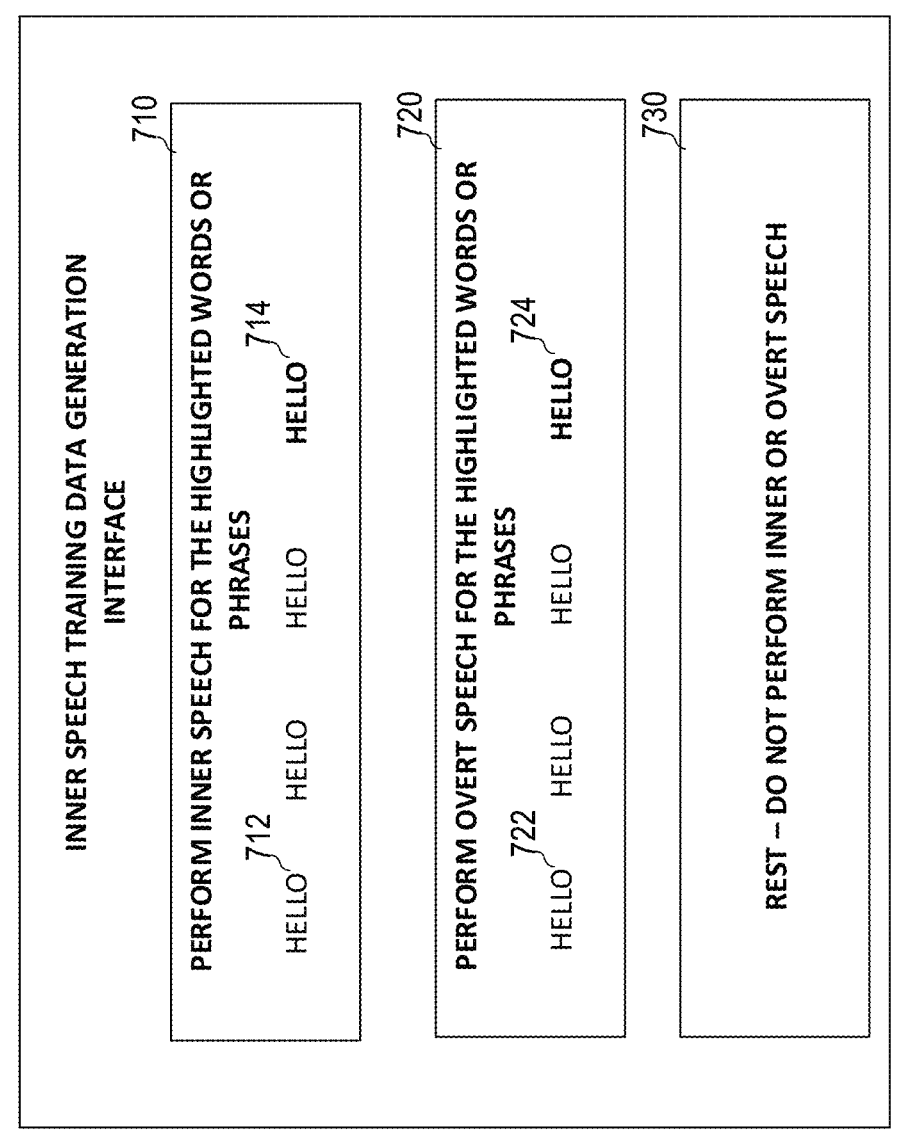
FIG. 7 is an illustrative output of the EMG speech detection system, in accordance with some examples.

The EMG data block processing module 620 can read blocks of EMG data received from the server in an asynchronous manner. Each block of EMG data is processed by the EMG data block processing module 620. A result of the EMG data block processing module 620 is a determination of whether inner speech was detected or is absent. Based on this decision, information is provided to the training data generation module 630 to generate inner speech training data based on the EMG signals (corresponding to inner speech, overt speech, and rest periods where no speech is being produced) processed by the EMG data block processing module 620. In some cases, the training data generation module 630 outputs instructions in a graphical user interface to instruct the user to produce inner speech, overt speech, and/or rest EMG signals. For example, the instructions can be presented in the user interface 700, shown in FIG. 7.

The EMG data block processing module 620 can include one or more of a noise reduction block, a feature extraction block, and a detection block. The feature extraction block computes informative features for inner speech detection from filtered EMG signals. In some examples, the square root of total energy of filtered EMG (such as the standard deviation of the block) is computed by the EMG data block processing module 620.

The training data generation module 630 generates instructions for one or more users to produce inner speech, overt speech, and rest-based EMG data. The training data generation module 630 collects data from the EMG data block processing module 620 corresponding to the inner speech, overt speech, and rest. Specifically, the training data generation module 630 stores a collection of different sets of identical phonemes, phoneme sounds, words or phrases. The training data generation module 630 generates a prompt for display to a user to produce inner speech or overt speech for a certain set of identical phonemes, phoneme sounds, words or phrases. In some cases, the training data generation module 630 first instructs the user to produce overt speech for an individual word. After collecting EMG data for the overt speech from the EMG data block processing module 620, the training data generation module 630 then instructs the user to produce inner speech for the same individual word. The training data generation module 630 collects the EMG data for the inner speech from the EMG data block processing module 620. The training data generation module 630 can also, prior to and/or after collecting the inner and/or overt speech EMG data, instruct the user to be quiet. While the user is quiet and not producing inner or overt speech, the training data generation module 630 collects EMG data representing rest-based EMG data from the EMG data block processing module 620. The training data generation module 630 can perform multiple iterations over multiple phonemes, phoneme sounds, words or phrases until a threshold quantity of sets of paired overt speech, inner speech, and rest EMG data is collected from the EMG data block processing module 620.

In some examples, the training data generation module 630 generates inner speech training data using the threshold quantity of sets of paired overt speech, inner speech, and rest EMG data collected from the EMG data block processing module 620. Specifically, the training data generation module 630 processes the threshold quantity of sets of paired overt speech, inner speech, and rest EMG data collected from the EMG data block processing module 620 to establish a relationship between the paired overt speech, inner speech, and rest EMVIG data. This relationship is used to compute transformation parameters for a transformation function. The training data generation module 630 then obtains a collection of overt speech-based EMG data (e.g., from one or more public sources on the Internet) and applies the transformation function to synthetically generate respective inner speech-based EMG data. The synthetically generated inner speech-based EMG data is paired with ground truth phonemes, phoneme sounds, words or phrases corresponding to the collection of overt speech-based EMG data. The training data generation module 630 generates training data using the paired synthetically generated inner speech-based EMG data and ground truth phonemes, phoneme sounds, words or phrases corresponding to the collection of overt speech-based EMG data.

In some examples, the training data generation module 630 provides the training data that includes the paired synthetically generated inner speech-based EMG data and ground truth phonemes, phoneme sounds, words or phrases corresponding to the collection of overt speech-based EMG data to the EMG data block processing module 620 to train one or more classifiers or ML models. Specifically, in each iteration of training, the EMG data block processing module 620 selects a portion of the inner speech training data that includes a set of EMG data representing synthetically generated inner speech corresponding to an individual word or phrase. The EMG data block processing module 620 processes the set of EMG data of the portion of the inner speech training data by the ML model to predict a word or phrase corresponding to the portion of the set of EMG data and computes a deviation between the predicted word or phrase and the individual word or phrase corresponding to the portion of the inner speech training data. The EMG data block processing module 620 updates one or more parameters of the ML model based on the computed deviation. This training process is repeated for a number of different training samples and/or until a stopping criterion is reached.

In some examples, the training data generation module 630 records various samples and pairs of overt speech EMG data, inner speech EMG data, and rest EMG data. To do so, the training data generation module 630 can present a user interface 700 (FIG. 7) to one or more users. In the example user interface 700, the training data generation module 630 includes an instruction in a first region 710 for collecting inner speech EMG data. Specifically, the training data generation module 630 selects an individual word (e.g., HELLO) and presents that word in the first region 710 as a target word 714. The training data generation module 630 can present an indicator that visually distinguishes the target word 714 from words 712 for which EMG data was previously collected. The indicator can include presenting the target word 714 in a red color and the words 712 in a black color. Once the target word 714 is highlighted, the user can begin producing inner speech for the target word 714. While the inner speech is being produced, the EMG data block processing module 620 collects EMG data and stores that EMG data in association with the target word 714 and inner speech.

Similarly, the training data generation module 630 can include an instruction in a second region 720 for collecting overt speech EMG data. Specifically, the training data generation module 630 selects an individual word (e.g., HELLO) and present that word in the second region 720 as a target word 724. The training data generation module 630 can present an indicator that visually distinguishes the target word 724 from words 722 for which EMG data was previously collected. The indicator can include presenting the target word 724 in a red color and the words 722 in a black color. Once the target word 724 is highlighted, the user can begin producing overt speech for the target word 724. While the overt speech is being produced, the EMG data block processing module 620 collects EMG data and stores that EMG data in association with the target word 714 and overt speech.

The training data generation module 630 can also collect rest-based EMG data. To do so, the training data generation module 630 can present an instruction in a third region 730. When the instruction is presented in the third region 730, the user remains quiet and does not produce any inner or overt speech. While the user is quiet, the EMG data block processing module 620 collects EMG data and stores that EMG data in association with rest-based EMG data. The training data generation module 630 generates a set of samples that include the inner speech and overt speech for the target word 714.

The training data generation module 630 can perform filtering and parsing for the recorded inner speech EMG data and overt speech EMG data. Specifically, the training data generation module 630 processes the recorded data to properly reference and filter using a standard pipeline for electrophysiological recordings, including high-pass filtering for drift removal and movement artifact removal, and line noise filtering. Then, the data is parsed to segments which may include no speech ("rest") or one or more utterances ("speech"). For example, the training data generation module 630 obtains a first portion of the samples including the inner speech EMG data. The training data generation module 630 applies high-pass filtering to the first portion of the samples to remove drift and artifacts and perform line noise filtering. Then, the training data generation module 630 uses the rest-based EMG data to segment the first portion of the samples into the segments that include inner speech and segments that do not include any inner or overt speech EMG data. Similarly, the training data generation module 630 obtains a second portion of the samples including the overt speech EMG data. The training data generation module 630 applies high-pass filtering to the second portion of the samples to remove drift and artifacts and perform line noise filtering. Then, the training data generation module 630 uses the rest-based EMG data to segment the second portion of the samples into the segments that include overt speech and segments that do not include any inner or overt speech EMG data.

In some examples, the training data generation module 630 performs speech activity detection and segment validation after performing filtering and parsing. To do so, the training data generation module 630, after parsing and filtering the samples, feeds segments of the samples into a signal validation block which tags time windows with speech activity and uses that information to determine whether the segment contains valid speech signals ("valid segment"). The training data generation module 630 detects activity in each segment by using the rest-based EMG data. Specifically, the training data generation module 630 uses "rest" segments to extract statistics about the noise level in the signal, including mean, standard deviation, minimum, and maximum, used in a subsequent thresholding step. These calibrated segments are used to learn the electrical noise profile, used in a subsequent noise reduction step. Statistics for thresholding are learned both on a per-channel basis and in aggregate basis across channels.

In some cases, the training data generation module 630 sets thresholds for speech detection. For example, the training data generation module 630 can set the activity detection threshold at two standard deviations above rest levels. Alternatively, rest trials and/or the extracted statistical features are used to train a statistical model for activity detection, whose output is a binary decision for each time window (activity detected/not detected). The electrical noise profile can learn a noise distribution of the rest signal and a noise mask can be learned and a stationary noise reduction algorithm can be applied. This helps improve the accuracy of activity detection.

After tagging the segments as containing or lacking speech signals, the training data generation module 630 performs a validation of the segments to indicate whether the segment is valid or invalid. Specifically, the training data generation module 630 requires that the active part of the segment be surrounded by inactive parts (no speech or rest EMG data). In some cases, the training data generation module 630 uses a 50 ms (milliseconds) rest period before activity onset and 250 ms rest period after activity offset. For example, the training data generation module 630 can obtain a sequence of segments. The training data generation module 630 identifies the speech detected portion of the segments and then determines whether a first rest period (e.g., 50 ms) precedes the speech detected portion and whether a second rest period (e.g., 250 ms) follows the speech detected portion. If so, the training data generation module 630 marks the segment as a valid speech segment. If speech is detected within one of the first or second rest periods, the sequence of segments can be discarded as invalid. The final step is aggregating across all windows and channels to arrive at a single decision for each segment (valid/invalid). The non-valid segments can be discarded.

In some examples, after generating a set of valid inner speech segments and valid overt speech segments that are paired with the inner speech segments, the training data generation module 630 establishes a relationship between these segments to compute one or more transformation parameters for a transformation function. The transformation function estimates the transformation parameters that need to be applied to modify EMG data corresponding to overt speech that estimates or matches the corresponding EMG data for inner speech.

Transformations and augmentations can be applied only to overt speech segments to predict or estimate inner speech segments. The transformation parameters may include one or more of scaling parameters, colored noise parameters, time shift parameters, and/or time warp parameters. The transformation parameters are applied to the entire overt speech segment, exclusively to parts of the overt speech segment where speech activity was detected, or exclusively to parts where no overt speech activity was detected.

For example, in the case of the scaling parameter, the training data generation module 630 computes the scaling factor based on any combination of the statistical parameters learned in the previous steps. Specifically, valid segments are used to extract descriptive statistics (mean, standard deviation (SD), minimum, maximum) of the active part, non-active part, and the entire segment for each individual segment of overt speech and inner speech. The training data generation module 630 computes a distribution of these values across all segments separately for overt and inner speech segments. The training data generation module 630 uses these distributions to calculate ratios. For example, in the case of the mean value during the active part of the segment, the ratio is computed as the mean of the "inner speech" root means square (RMS) distribution divided by the mean of the "overt speech" RMS distribution. In some cases, a central RMS value of 0.36 and a range of plus minus 10% can be used. In general, the training data generation module 630 computes the scaling parameter as a ratio of the EMG data corresponding to the overt speech activity portion of a segment and EMG data corresponding to the inner speech activity portion of a segment. This scaling parameter can then be used to transform a new overt speech EMG data portion to a synthetic inner speech EMG data portion.

In some examples, the training data generation module 630 adds colored noise (e.g., using a colored noise parameter) after scaling with the goal of matching the signal-to-noise (SNR) of the overt speech with the learned SNR for inner speech. The noise profile (signal characteristics during non-active parts of the segment) may not be "white" or random and is learned from the "rest" segments on a per-channel basis. Noise power can be set to restore the noise level before scaling, with $\sigma syn=\sqrt{(1-\alpha 2)}\sigma$, where a is the scaling level and a is the session noise level. In general, the training data generation module 630 computes the colored noise parameter as a ratio of the SNR corresponding to the EMG data of overt speech activity portion of a segment and SNR data corresponding to the EMG data of inner speech activity portion of a segment. This colored noise parameter can then be used to transform a new overt speech EMG data portion to a synthetic inner speech EMG data portion.

In some examples, the training data generation module 630 generates a time shift and time warp parameter(s). These time shift and time warp parameter(s) can be used to stretch or compress EMG data for overt speech into EMG data for synthesized inner speech. These time shift and time warp parameter(s) can be computed based on measuring a relationship between known samples of time shift and time warp between overt speech EMG data and inner speech EMG data. In some examples, the time warp transformation stretches or compresses the signal in time and use a time warp central value of 1.3 plus/minus 0.15. In some examples, the time shift transformation shifts (moves) the signal in time by a specified value, such as using by moving the signal relative to an original starting point according to a time shift value of −0.2 seconds to 0.2 seconds around an original zero point.

The training data generation module 630 can apply fuzziness and spectrum to any one of the transformation parameters. For example, the training data generation module 630 generates multiple inner speech training data samples from the same overt speech EMG data by adjusting values of the transformation parameters. In some examples, the training data generation module 630 generates different ranges of values for each of the transformation parameters and then randomly selects an individual transformation parameter value from the range. The selected individual transformation parameter value can then be used to adjust overt speech EMG data to generate inner speech EMG data. For example, the training data generation module 630 can obtain a central value for the scaling parameter and can generate a range of about 20% plus or minus around that central value. The training data generation module 630 selects a random scaling parameter value from the generated range to form a first transformation parameter of the transformation function. Similarly, the training data generation module 630 obtains a central value for the colored noise parameter and can generate a range of about 20% plus or minus around that central value. The training data generation module 630 selects a random colored noise parameter value from the generated range to form a second transformation parameter of the transformation function. Similarly, the training data generation module 630 obtains central values for the time shift and time warp parameters and can generate a range of about 20% plus or minus around that central value. The training data generation module 630 selects random time shift and time warp parameter values from the generated range to form the third and fourth transformation parameters of the transformation function.

The training data generation module 630 can obtain a set of EMG data corresponding to overt speech and apply the first, second, and third transformation parameters of the transformation function to the set of EMG data corresponding to overt speech to generate synthetically a first sample of EMG data corresponding to inner speech associated with the overt speech (for a particular word or phase). The training data generation module 630 selects a second random scaling parameter value from the generated range to adjust the first transformation parameter of the transformation function; a second random colored noise parameter value from the generated range to adjust the second transformation parameter of the transformation function; and/or a second random time shift/time warp parameter value from the generated range to adjust the third transformation parameter of the transformation function. The training data generation module 630 obtains the set of EMG data corresponding to overt speech and apply the adjusted first, adjusted second, and adjusted third transformation parameters of the transformation function to the set of EMG data corresponding to overt speech to synthetically generate a second sample of EMG data corresponding to inner speech associated with the overt speech (for the same particular word or phrase). After multiple iterations across different sets of EMG data of different overt speech samples using various values of the transformation function, various collections of synthetically generated inner speech EMG data are formed and used to train the EMG data block processing module 620.

After the EMG data block processing module 620 completes being trained using the synthetic inner speech training data, the EMG data block processing module 620 can be applied to real time inner speech EMG data to predict one or more phonemes, phoneme sounds, words or phrases corresponding to the inner speech EMG data. The EMG data block processing module 620 provides those predictions to the operation trigger module 640 to control operations of the user system 102 and/or interaction client 104.

FIG. 8 is a flowchart of a process 800 or method performed by the EMG speech detection system 600, in accordance with some examples. Although the flowchart can describe the operations as a sequential process, many of the operations can be performed in parallel or concurrently. In addition, the order of the operations may be re-arranged. A process is terminated when its operations are completed. A process may correspond to a method, a procedure, and the like. The steps or methods may be performed in whole or in part, may be performed in conjunction with some or all of the steps in other methods, and may be performed by any number of different systems or any portion thereof, such as a processor included in any of the systems.

At operation 801, the EMG speech detection system 600 (e.g., a user system 102 or a server) accesses a collection of overt speech signals representing phonemes, phoneme sounds, words or phrases spoken at least partially using overt speech, as discussed above.

At operation 802, the EMG speech detection system 600 transforms the collection of overt speech signals into inner speech training data comprising EMG data representing inner speech corresponding to the phonemes, phoneme sounds, words or phrases spoken at least partially using the overt speech, as discussed above.

At operation 803, the EMG speech detection system 600 trains a machine learning model to decode inner speech signals into a set of corresponding phonemes, phoneme sounds, words or phrases based on the inner speech training data, as discussed above.

Machine Architecture

Figure 9:
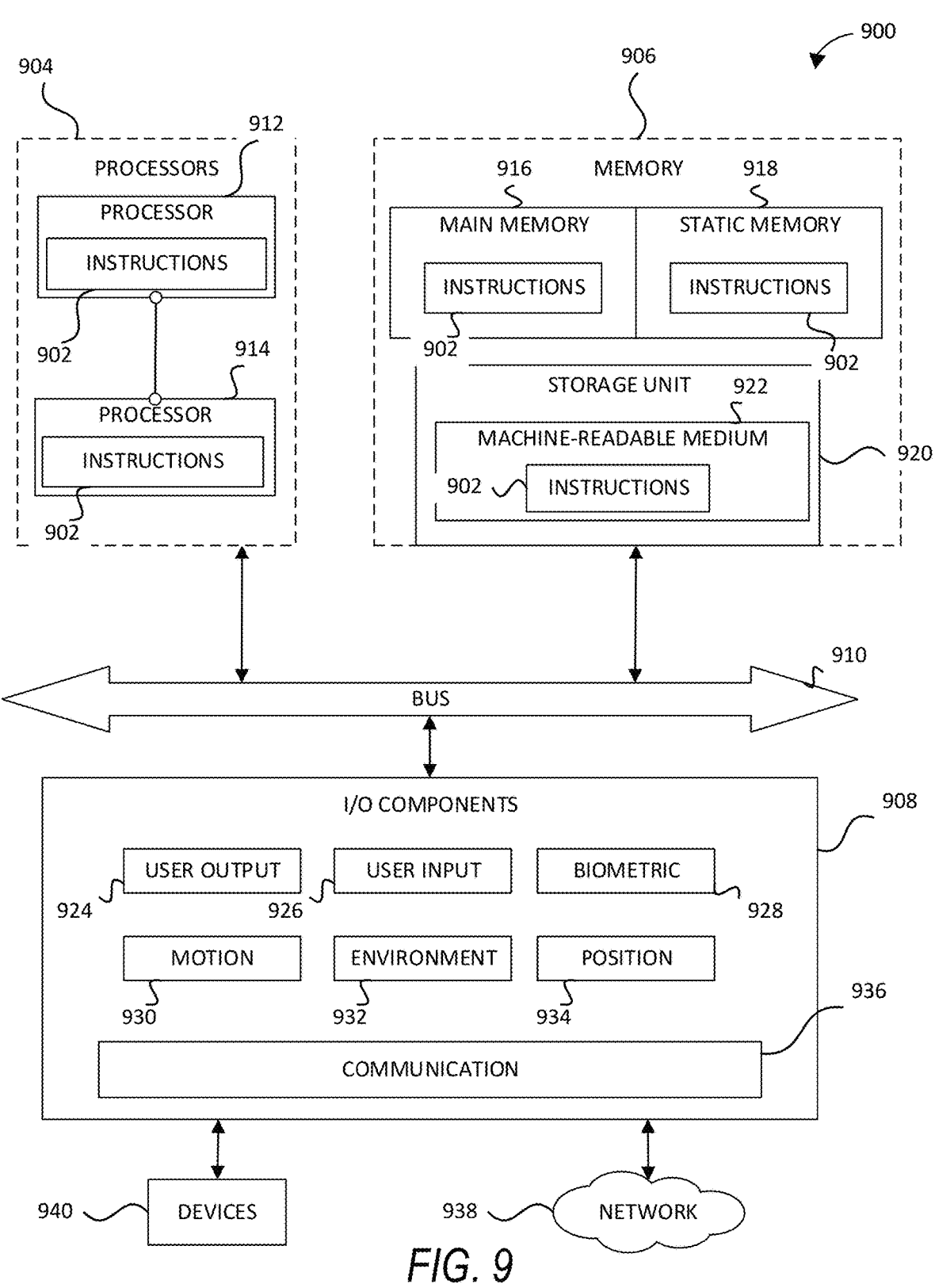
FIG. 9 is a diagrammatic representation of a machine in the form of a computer system within which a set of instructions may be executed to cause the machine to perform any one or more of the methodologies discussed herein, according to some examples.

FIG. 9 is a diagrammatic representation of the machine 900 within which instructions 902 (e.g., software, a program, an application, an applet, an app, or other executable code) for causing the machine 900 to perform any one or more of the methodologies discussed herein may be executed. For example, the instructions 902 may cause the machine 900 to execute any one or more of the methods described herein. The instructions 902 transform the general, non-programmed machine 900 into a particular machine 900 programmed to carry out the described and illustrated functions in the manner described. The machine 900 may operate as a standalone device or may be coupled (e.g., networked) to other machines. In a networked deployment, the machine 900 may operate in the capacity of a server machine or a client machine in a server-client network environment, or as a peer machine in a peer-to-peer (or distributed) network environment. The machine 900 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 902, sequentially or otherwise, that specify actions to be taken by the machine 900. Further, while a single machine 900 is illustrated, the term "machine" shall also be taken to include a collection of machines that individually or jointly execute the instructions 902 to perform any one or more of the methodologies discussed herein. The machine 900, for example, may comprise the user system 102 or any one of multiple server devices forming part of the interaction server system 110. In some examples, the machine 900 may also comprise both client and server systems, with certain operations of a particular method or algorithm being performed on the server-side and with certain operations of the particular method or algorithm being performed on the client-side.

The machine 900 may include processors 904, memory 906, and input/output (I/O) components 908, which may be configured to communicate with each other via a bus 910. In an example, the processors 904 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 912 and a processor 914 that execute the instructions 902. The term "processor" is intended to include multi-core processors that may comprise two or more independent processors (sometimes referred to as "cores") that may execute instructions contemporaneously. Although FIG. 9 shows multiple processors 904, the machine 900 may include a single processor with a single-core, a single processor with multiple cores (e.g., a multi-core processor), multiple processors with a single core, multiple processors with multiples cores, or any combination thereof.

The memory 906 includes a main memory 916, a static memory 918, and a storage unit 920, both accessible to the processors 904 via the bus 910. The main memory 906, the static memory 918, and storage unit 920 store the instructions 902 embodying any one or more of the methodologies or functions described herein. The instructions 902 may also reside, completely or partially, within the main memory 916, within the static memory 918, within machine-readable medium 922 within the storage unit 920, within at least one of the processors 904 (e.g., within the processor's cache memory), or any suitable combination thereof, during execution thereof by the machine 900.

The I/O components 908 may include a wide variety of components to receive input, provide output, produce output, transmit information, exchange information, capture measurements, and so on. The specific I/O components 908 that are included in a particular machine will depend on the type of machine. For example, portable machines such as mobile phones may include a touch input device or other such input mechanisms, while a headless server machine will likely not include such a touch input device. It will be appreciated that the I/O components 908 may include many other components that are not shown in FIG. 9. In various examples, the I/O components 908 may include user output components 924 and user input components 926. The user output components 924 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 926 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like. Any biometric collected by the biometric components is captured and stored with user approval and deleted on user request. Further, such biometric data may be used for very limited purposes, such as identification verification. To ensure limited and authorized use of biometric information and other personally identifiable information (PII), access to this data is restricted to authorized personnel only, if allowed at all. Any use of biometric data may strictly be limited to identification verification purposes, and the data is not shared or sold to any third party without the explicit consent of the user. In addition, appropriate technical and organizational measures are implemented to ensure the security and confidentiality of this sensitive information.

In further examples, the I/O components 908 may include biometric components 928, motion components 930, environmental components 932, or position components 934, among a wide array of other components. For example, the biometric components 928 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The biometric components may include a brain-machine interface (BMI) system that allows communication between the brain and an external device or machine. This may be achieved by recording brain activity data, translating this data into a format that can be understood by a computer, and then using the resulting signals to control the device or machine.

Example types of BMI technologies include:

Electroencephalography (EEG) based BMIs, which record electrical activity in the brain using electrodes placed on the scalp.

Invasive BMIs, which use electrodes that are surgically implanted into the brain.

Optogenetics BMIs, which use light to control the activity of specific nerve cells in the brain.

Any biometric data collected by the biometric components is captured and stored only with user approval and deleted on user request. Further, such biometric data may be used for very limited purposes, such as identification verification. To ensure limited and authorized use of biometric information and other personally identifiable information (PII), access to this data is restricted to authorized personnel only, if allowed at all. Any use of biometric data may strictly be limited to identification verification purposes, and the data is not shared or sold to any third party without the explicit consent of the user. In addition, appropriate technical and organizational measures are implemented to ensure the security and confidentiality of this sensitive information.

The motion components 930 include acceleration sensor components (e.g., accelerometer), gravitation sensor components, and rotation sensor components (e.g., gyroscope).

The environmental components 932 include, for example, one or more cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the user system 102 may have a camera system comprising, for example, front cameras on a front surface of the user system 102 and rear cameras on a rear surface of the user system 102. The front cameras may, for example, be used to capture still images and video of a user of the user system 102 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the user system 102 may also include a 3600 camera for capturing 360° photographs and videos.

Further, the camera system of the user system 102 may include dual rear cameras (e.g., a primary camera as well as a depth-sensing camera), or even triple, quad or penta rear camera configurations on the front and rear sides of the user system 102. These multiple cameras systems may include a wide camera, an ultra-wide camera, a telephoto camera, a macro camera, and a depth sensor, for example.

The position components 934 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 908 further include communication components 936 operable to couple the machine 900 to a network 938 or devices 940 via respective coupling or connections. For example, the communication components 936 may include a network interface component or another suitable device to interface with the network 938. In further examples, the communication components 936 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 940 may be another machine or any of a wide variety of peripheral devices (e.g., a peripheral device coupled via a USB).

Moreover, the communication components 936 may detect identifiers or include components operable to detect identifiers. For example, the communication components 936 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph™, MaxiCode, PDF417, Ultra Code, UCC RSS-2D bar code, and other optical codes), or acoustic detection components (e.g., microphones to identify tagged audio signals). In addition, a variety of information may be derived via the communication components 936, such as location via Internet Protocol (IP) geolocation, location via Wi-Fi® signal triangulation, location via detecting an NFC beacon signal that may indicate a particular location, and so forth.

The various memories (e.g., main memory 916, static memory 918, and memory of the processors 904) and storage unit 920 may store one or more sets of instructions and data structures (e.g., software) embodying or used by any one or more of the methodologies or functions described herein. These instructions (e.g., the instructions 902), when executed by processors 904, cause various operations to implement the disclosed examples.

The instructions 902 may be transmitted or received over the network 938, using a transmission medium, via a network interface device (e.g., a network interface component included in the communication components 936) and using any one of several well-known transfer protocols (e.g., hypertext transfer protocol (HTTP)). Similarly, the instructions 902 may be transmitted or received using a transmission medium via a coupling (e.g., a peer-to-peer coupling) to the devices 940.

Software Architecture

Figure 10:
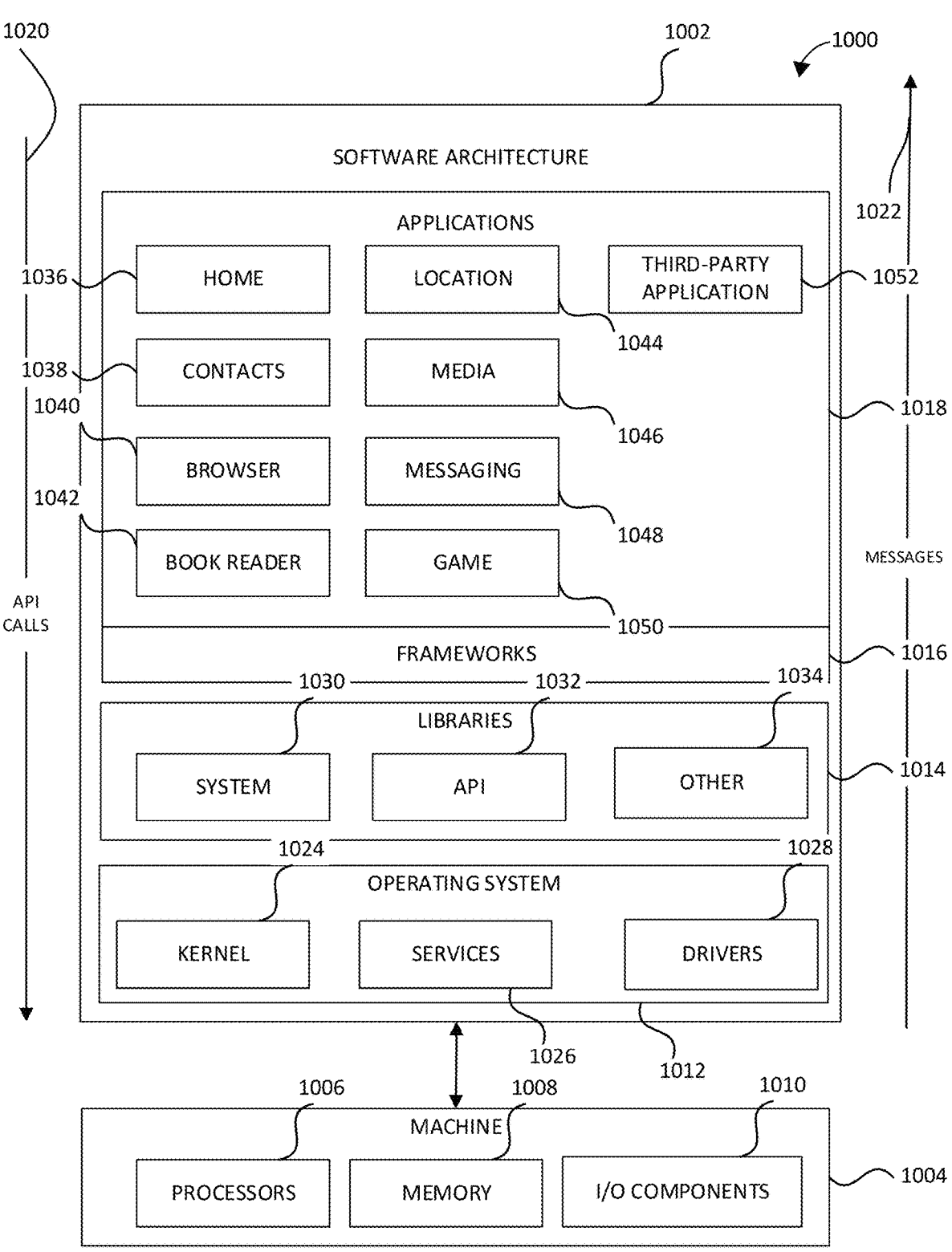
FIG. 10 is a block diagram showing a software architecture within which examples may be implemented.

FIG. 10 is a block diagram 1000 illustrating a software architecture 1002, which can be installed on any one or more of the devices described herein. The software architecture 1002 is supported by hardware such as a machine 1004 that includes processors 1006, memory 1008, and I/O components 1010. In this example, the software architecture 1002 can be conceptualized as a stack of layers, where each layer provides a particular functionality. The software architecture 1002 includes layers such as an operating system 1012, libraries 1014, frameworks 1016, and applications 1018. Operationally, the applications 1018 invoke API calls 1020 through the software stack and receive messages 1022 in response to the API calls 1020.

The operating system 1012 manages hardware resources and provides common services. The operating system 1012 includes, for example, a kernel 1024, services 1026, and drivers 1028. The kernel 1024 acts as an abstraction layer between the hardware and the other software layers. For example, the kernel 1024 provides memory management, processor management (e.g., scheduling), component management, networking, and security settings, among other functionalities. The services 1026 can provide other common services for the other software layers. The drivers 1028 are responsible for controlling or interfacing with the underlying hardware. For instance, the drivers 1028 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1014 provide a common low-level infrastructure used by the applications 1018. The libraries 1014 can include system libraries 1030 (e.g., C standard library) that provide functions such as memory allocation functions, string manipulation functions, mathematic functions, and the like. In addition, the libraries 1014 can include API libraries 1032 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1014 can also include a wide variety of other libraries 1034 to provide many other APIs to the applications 1018.

The frameworks 1016 provide a common high-level infrastructure that is used by the applications 1018. For example, the frameworks 1016 provide various graphical user interface (GUI) functions, high-level resource management, and high-level location services. The frameworks 1016 can provide a broad spectrum of other APIs that can be used by the applications 1018, some of which may be specific to a particular operating system or platform.

In an example, the applications 1018 may include a home application 1036, a contacts application 1038, a browser application 1040, a book reader application 1042, a location application 1044, a media application 1046, a messaging application 1048, a game application 1050, and a broad assortment of other applications such as a third-party application 1052. The applications 1018 are programs that execute functions defined in the programs. Various programming languages can be employed to create one or more of the applications 1018, structured in a variety of manners, such as object-oriented programming languages (e.g., Objective-C, Java, or C++) or procedural programming languages (e.g., C or assembly language). In a specific example, the third-party application 1052 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 1052 can invoke the API calls 1020 provided by the operating system 1012 to facilitate functionalities described herein.

System with Head-Wearable Apparatus

Figure 11:
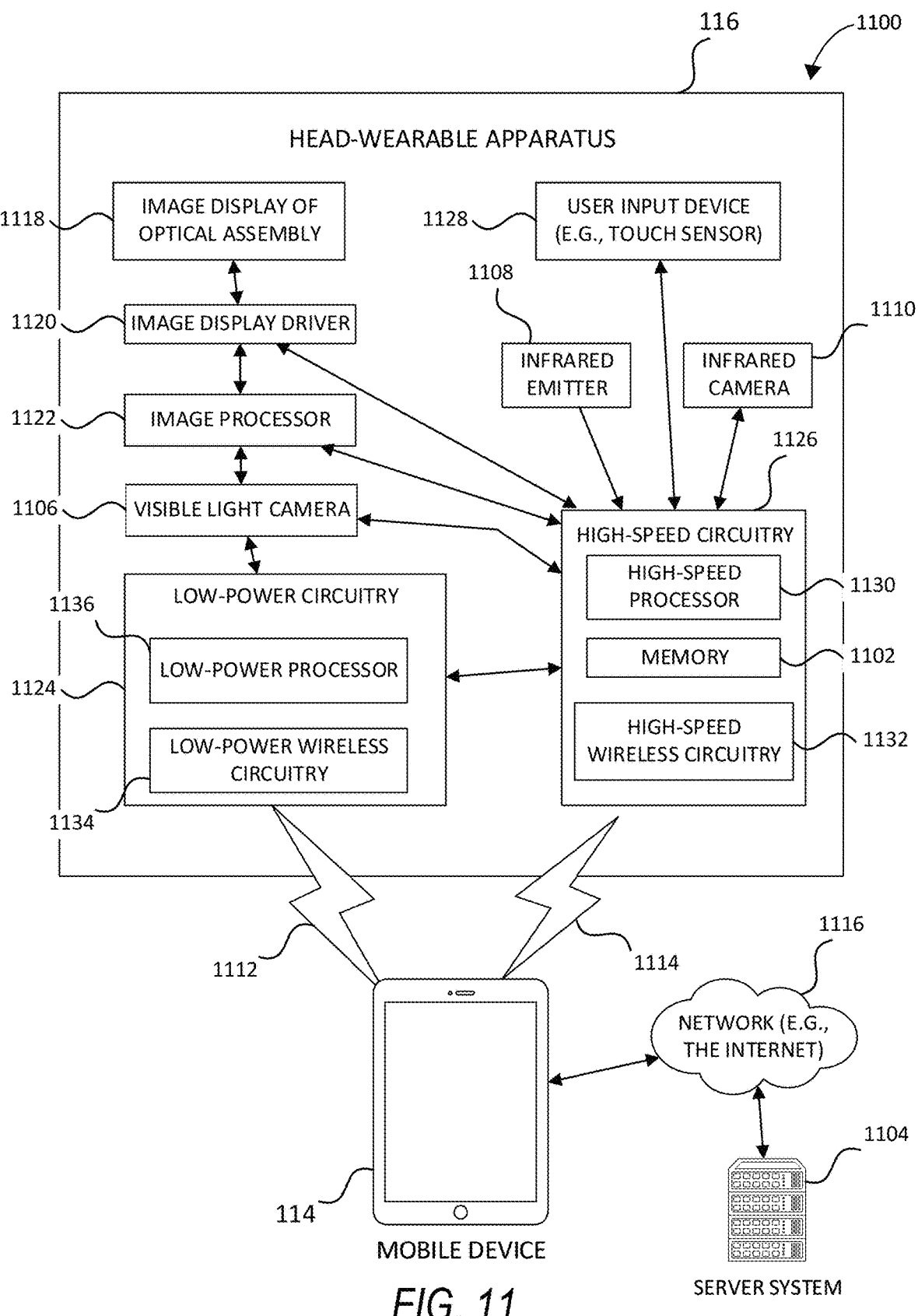
FIG. 11 illustrates a system in which a head-wearable apparatus may be implemented, according to some examples.

FIG. 11 illustrates a system 1100 including a head-wearable apparatus 116 with a selector input device, according to some examples. FIG. 11 is a high-level functional block diagram of an example head-wearable apparatus 116 communicatively coupled to a mobile device 114 and various server systems 1104 (e.g., the interaction server system 110) via various networks 108.

The head-wearable apparatus 116 includes one or more cameras, each of which may be, for example, a visible light camera 1106, an infrared emitter 1108, and an infrared camera 1110.

The mobile device 114 connects with head-wearable apparatus 116 using both a low-power wireless connection 1112 and a high-speed wireless connection 1114. The mobile device 114 is also connected to the server system 1104 and the network 1116.

The head-wearable apparatus 116 further includes two image displays of the image display of optical assembly 1118. The two image displays of optical assembly 1118 include one associated with the left lateral side and one associated with the right lateral side of the head-wearable apparatus 116. The head-wearable apparatus 116 also includes an image display driver 1120, an image processor 1122, low-power circuitry 1124, and high-speed circuitry 1126. The image display of optical assembly 1118 is for presenting images and videos, including an image that can include a graphical user interface, to a user of the head-wearable apparatus 116.

The image display driver 1120 commands and controls the image display of optical assembly 1118. The image display driver 1120 may deliver image data directly to the image display of optical assembly 1118 for presentation or may convert the image data into a signal or data format suitable for delivery to the image display device. For example, the image data may be video data formatted according to compression formats, such as H.264 (MPEG-4 Part 10), HEVC, Theora, Dirac, RealVideo RV40, VP8, VP9, or the like, and still image data may be formatted according to compression formats such as Portable Network Group (PNG), Joint Photographic Experts Group (JPEG), Tagged Image File Format (TIFF) or exchangeable image file format (EXIF) or the like.

The head-wearable apparatus 116 includes a frame and stems (or temples) extending from a lateral side of the frame. The head-wearable apparatus 116 further includes a user input device 1128 (e.g., touch sensor or push button), including an input surface on the head-wearable apparatus 116. The user input device 1128 (e.g., touch sensor or push button) is to receive from the user an input selection to manipulate the graphical user interface of the presented image.

The components shown in FIG. 11 for the head-wearable apparatus 116 are located on one or more circuit boards, for example a PCB or flexible PCB, in the rims or temples. Alternatively, or additionally, the depicted components can be located in the chunks, frames, hinges, or bridge of the head-wearable apparatus 116. Left and right visible light cameras 1106 can include digital camera elements such as a complementary metal oxide-semiconductor (CMOS) image sensor, charge-coupled device, camera lenses, or any other respective visible or light-capturing elements that may be used to capture data, including images of scenes with unknown objects.

The head-wearable apparatus 116 includes a memory 1102, which stores instructions to perform a subset or all of the functions described herein. The memory 1102 can also include a storage device.

As shown in FIG. 11, the high-speed circuitry 1126 includes a high-speed processor 1130, a memory 1102, and high-speed wireless circuitry 1132. In some examples, the image display driver 1120 is coupled to the high-speed circuitry 1126 and operated by the high-speed processor 1130 in order to drive the left and right image displays of the image display of optical assembly 1118. The high-speed processor 1130 may be any processor capable of managing high-speed communications and operation of any general computing system needed for the head-wearable apparatus 116. The high-speed processor 1130 includes processing resources needed for managing high-speed data transfers on a high-speed wireless connection 1114 to a wireless local area network (WLAN) using the high-speed wireless circuitry 1132. In certain examples, the high-speed processor 1130 executes an operating system such as a LINUX operating system or other such operating system of the head-wearable apparatus 116, and the operating system is stored in the memory 1102 for execution. In addition to any other responsibilities, the high-speed processor 1130 executing a software architecture for the head-wearable apparatus 116 is used to manage data transfers with high-speed wireless circuitry 1132. In certain examples, the high-speed wireless circuitry 1132 is configured to implement Institute of Electrical and Electronic Engineers (IEEE) 802.11 communication standards, also referred to herein as WiFi. In some examples, other high-speed communications standards may be implemented by the high-speed wireless circuitry 1132.

The low-power wireless circuitry 1134 and the high-speed wireless circuitry 1132 of the head-wearable apparatus 116 can include short-range transceivers (Bluetooth™) and wireless wide, local, or wide area network transceivers (e.g., cellular or WiFi). Mobile device 114, including the transceivers communicating via the low-power wireless connection 1112 and the high-speed wireless connection 1114, may be implemented using details of the architecture of the head-wearable apparatus 116, as can other elements of the network 1116.

The memory 1102 includes any storage device capable of storing various data and applications, including, among other things, camera data generated by the left and right visible light cameras 1106, the infrared camera 1110, and the image processor 1122, as well as images generated for display by the image display driver 1120 on the image displays of the image display of optical assembly 1118. While the memory 1102 is shown as integrated with high-speed circuitry 1126, in some examples, the memory 1102 may be an independent standalone element of the head-wearable apparatus 116. In certain such examples, electrical routing lines may provide a connection through a chip that includes the high-speed processor 1130 from the image processor 1122 or the low-power processor 1136 to the memory 1102. In some examples, the high-speed processor 1130 may manage addressing of the memory 1102 such that the low-power processor 1136 will boot the high-speed processor 1130 any time that a read or write operation involving memory 1102 is needed.

As shown in FIG. 11, the low-power processor 1136 or high-speed processor 1130 of the head-wearable apparatus 116 can be coupled to the camera (visible light camera 1106, infrared emitter 1108, or infrared camera 1110), the image display driver 1120, the user input device 1128 (e.g., touch sensor or push button), and the memory 1102.

The head-wearable apparatus 116 is connected to a host computer. For example, the head-wearable apparatus 116 is paired with the mobile device 114 via the high-speed wireless connection 1114 or connected to the server system 1104 via the network 1116. The server system 1104 may be one or more computing devices as part of a service or network computing system, for example, that includes a processor, a memory, and network communication interface to communicate over the network 1116 with the mobile device 114 and the head-wearable apparatus 116.

The mobile device 114 includes a processor and a network communication interface coupled to the processor. The network communication interface allows for communication over the network 1116, low-power wireless connection 1112, or high-speed wireless connection 1114. Mobile device 114 can further store at least portions of the instructions for generating binaural audio content in the mobile device 114's memory to implement the functionality described herein.

Output components of the head-wearable apparatus 116 include visual components, such as a liquid crystal display (LCD), a plasma display panel (PDP), a light-emitting diode (LED) display, a projector, or a waveguide. The image displays of the optical assembly are driven by the image display driver 1120. The output components of the head-wearable apparatus 116 further include acoustic components (e.g., speakers), haptic components (e.g., a vibratory motor), other signal generators, and so forth. The input components of the head-wearable apparatus 116, the mobile device 114, and server system 1104, such as the user input device 1128, may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

The head-wearable apparatus 116 may also include additional peripheral device elements. Such peripheral device elements may include biometric sensors, additional sensors, or display elements integrated with the head-wearable apparatus 116. For example, peripheral device elements may include any I/O components including output components, motion components, position components, or any other such elements described herein.

For example, the biometric components include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The biometric components may include a brain-machine interface (BMI) system that allows communication between the brain and an external device or machine. This may be achieved by recording brain activity data, translating this data into a format that can be understood by a computer, and then using the resulting signals to control the device or machine.

Example types of BMI technologies include:

Electroencephalography (EEG) based BMIs, which record electrical activity in the brain using electrodes placed on the scalp.

Invasive BMIs, which use electrodes that are surgically implanted into the brain.

Optogenetics BMIs, which use light to control the activity of specific nerve cells in the brain.

Any biometric data collected by the biometric components is captured and stored only with user approval and deleted on user request. Further, such biometric data may be used for very limited purposes, such as identification verification. To ensure limited and authorized use of biometric information and other personally identifiable information (PII), access to this data is restricted to authorized personnel only, if allowed at all. Any use of biometric data may strictly be limited to identification verification purposes, and the biometric data is not shared or sold to any third party without the explicit consent of the user. In addition, appropriate technical and organizational measures are implemented to ensure the security and confidentiality of this sensitive information.

The motion components include acceleration sensor components (e.g., accelerometer), gravitation sensor components, rotation sensor components (e.g., gyroscope), and so forth. The position components include location sensor components to generate location coordinates (e.g., a Global Positioning System (GPS) receiver component), Wi-Fi or Bluetooth™ transceivers to generate positioning system coordinates, altitude sensor components (e.g., altimeters or barometers that detect air pressure from which altitude may be derived), orientation sensor components (e.g., magnetometers), and the like. Such positioning system coordinates can also be received over low-power wireless connections 1112 and high-speed wireless connection 1114 from the mobile device 114 via the low-power wireless circuitry 1134 or high-speed wireless circuitry 1132.

EXAMPLES

Example 1. A method comprising: accessing a collection of overt speech signals representing phonemes, phoneme sounds, words or phrases spoken at least partially using overt speech; transforming the collection of overt speech signals into inner speech training data comprising electromyograph (EMG) data representing inner speech corresponding to the phonemes, phoneme sounds, words or phrases spoken at least partially using the overt speech; and training a machine learning model to decode inner speech signals into a set of corresponding phonemes, phoneme sounds, words or phrases based on the inner speech training data.

Example 2. The method of Example 1, further comprising: selecting a portion of the inner speech training data comprising a set of EMG data representing inner speech corresponding to an individual word or phrase; processing the set of EMG data of the portion of the inner speech training data by the machine learning model to predict a word or phrase corresponding to the portion of the set of EMG data; computing a deviation between the predicted word or phrase and the individual word or phrase corresponding to the portion of the inner speech training data; and updating one or more parameters of the machine learning model based on the computed deviation.

Example 3. The method of any one of Examples 1-2, further comprising: obtaining a first training set of overt speech segments corresponding to a training set of phonemes, phoneme sounds, words or phrases; obtaining a second training set of inner speech segments corresponding to the training set of phonemes, phoneme sounds, words or phrases; obtaining a third training set of rest data representing a portion when inner or overt speech signals are not being produced; and establishing a relationship between EMG data corresponding to the first training set of overt speech segments, EMG data corresponding to the second training set of inner speech segments, and the third training set of rest data.

Example 4. The method of Example 3, further comprising: computing one or more transformation parameters based on the established relationship between the EMG data corresponding to the first training set of overt speech segments, the EMG data corresponding to the second training set of inner speech segments, and the third training set of rest data.

Example 5. The method of Example 4, wherein transforming the collection of overt speech signals into the inner speech training data is based on the one or more transformation parameters.

Example 6. The method of any one of Examples 3-5, further comprising: retrieving the EMG data corresponding to the first training set of overt speech segments; and filtering the EMG data corresponding to the first training set of overt speech segments to remove drift and artifacts.

Example 7. The method of any one of Examples 3-6, further comprising: retrieving the EMG data corresponding to the second training set of inner speech segments; and filtering the EMG data corresponding to the second training set of inner speech segments to remove drift and artifacts.

Example 8. The method of any one of Examples 3-7, further comprising: processing the EMG data corresponding to the first training set of overt speech segments to tag time windows representing presence of speech activity; processing the EMG data corresponding to the second training set of inner speech segments to tag time windows representing presence of speech activity; validating the EMG data corresponding to the first training set of overt speech segments based on the tagged time windows of the first training set of overt speech segments; and validating the EMG data corresponding to the second training set of inner speech segments based on the tagged time windows of the second training set of inner speech segments.

Example 9. The method of Example 8, wherein validating the EMG data corresponding to the first training set of overt speech segments comprises: determining that a first portion of the EMG data corresponding to a first portion of the first training set of overt speech segments is between a first rest period and a second rest period; and in response to determining that the first portion of the EMG data is between the first rest period and the second rest period, marking the first portion of the first training set of overt speech segments as valid.

Example 10. The method of Example 9, further comprising: determining that a second portion of the EMG data corresponding to a second portion of the first training set of overt speech segments is during at least one of the first rest period or the second rest period; and in response to determining that the second portion of the EMG data is during at least one of the first rest period or the second rest period, marking the second portion the first training set of overt speech segments as invalid. Specifically, a segment can be marked as in valid if its activity interval is not surrounded by 50 ms rest period in the start, and 250 ms rest period in the end.

Example 11. The method of any one of Examples 8-10, wherein validating the EMG data corresponding to the second training set of inner speech segments comprises: determining that a first portion of the EMG data corresponding to a first portion of the second training set of inner speech segments is between a first rest period and a second rest period; and in response to determining that the first portion of the EMG data is between the first rest period and the second rest period, marking the first portion of the second training set of inner speech segments as valid.

Example 12. The method of Example 11, further comprising: determining that a second portion of the EMG data corresponding to a second portion of the second training set of inner speech segments is during at least one of the first rest period or the second rest period; and in response to determining that the second portion of the EMG data is during at least one of the first rest period or the second rest period, marking the second portion the second training set of inner speech segments as invalid.

Example 13. The method of any one of Examples 9-12, wherein the second rest period is longer than the first rest period.

Example 14. The method of any one of Examples 8-13, wherein presence of speech activity is detected by determining that a signal level in the EMG data corresponding to the first training set of overt speech segments is greater than a noise level associated with the third training set of rest data by a threshold amount. In such cases, the EMG data corresponding to the first training set of overt speech segments is filtered to remove drift and artifacts Example 15. The method of any one of Examples 3-14, further comprising: computing a scaling parameter representing a ratio of the EMG data corresponding to the first training set of overt speech segments to the EMG data corresponding to the second training set of inner speech segments; computing a colored noise parameter that matches a signal to noise (SNR) of the EMG data corresponding to the first training set of overt speech segments to the SNR of the EMG data corresponding to the second training set of inner speech segments based on a noise profile determined using the third training set of rest data; computing a time shift parameter for adjusting the onset of EMG data corresponding to overt speech; and computing a time warp parameter for stretching or compressing EMG data corresponding to overt speech.

Example 16. The method of Example 15, further comprising: adjusting the scaling parameter by a first random value drawn from a first specified range around a value of the scaling parameter; adjusting the colored noise parameter by a second random value drawn from a second specified range around a value of the colored noise parameter; and adjusting the time shift parameter by a third random value drawn from a third specified range around a value of the time shift parameter.

Example 17. The method of Example 16, further comprising: modifying EMG data corresponding to the collection of overt speech signals using the adjusted scaling parameter, the adjusted colored noise parameter, and the adjusted time shift parameter to generate a first portion of the inner speech training data.

Example 18. The method of Example 17, further comprising: re-adjusting the scaling parameter, colored noise parameter, and the time shift parameter by additional random values drawn respectively from the first specified range, second specified range, and third specified range; and modifying EMG data corresponding to the collection of overt speech signals using the re-adjusted scaling parameter, the re-adjusted colored noise parameter, and the re-adjusted time shift parameter to generate a second portion of the inner speech training data.

Example 19. A system comprising: at least one processor; and at least one memory component having instructions stored thereon that, when executed by the at least one processor, cause the at least one processor to perform operations comprising: accessing a collection of overt speech signals representing phonemes, phoneme sounds, words or phrases spoken at least partially using overt speech; transforming the collection of overt speech signals into inner speech training data comprising electromyograph (EMG) data representing inner speech corresponding to the phonemes, phoneme sounds, words or phrases spoken at least partially using the overt speech; and training a machine learning model to decode inner speech signals into a set of corresponding phonemes, phoneme sounds, words or phrases based on the inner speech training data.

Example 20. A non-transitory computer-readable storage medium having stored thereon instructions that, when executed by at least one processor, cause the at least one processor to perform operations comprising: accessing a collection of overt speech signals representing phonemes, phoneme sounds, words or phrases spoken at least partially using overt speech; transforming the collection of overt speech signals into inner speech training data comprising electromyograph (EMG) data representing inner speech corresponding to the phonemes, phoneme sounds, words or phrases spoken at least partially using the overt speech; and training a machine learning model to decode inner speech signals into a set of corresponding phonemes, phoneme sounds, words or phrases based on the inner speech training data.

Glossary

"Carrier signal" refers, for example, to any intangible medium that is capable of storing, encoding, or carrying instructions for execution by the machine and includes digital or analog communications signals or other intangible media to facilitate communication of such instructions. Instructions may be transmitted or received over a network using a transmission medium via a network interface device.

"Client device" refers, for example, to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers, for example, to one or more portions of a network that may be an ad hoc network, an intranet, an extranet, a virtual private network (VPN), a local area network (LAN), a wireless LAN (WLAN), a wide area network (WAN), a wireless WAN (WWAN), a metro-politan area network (MAN), the Internet, a portion of the Internet, a portion of the Public Switched Telephone Net-work (PSTN), a plain old telephone service (POTS) net-work, a cellular telephone network, a wireless network, a Wi-Fi® network, another type of network, or a combination of two or more such networks. For example, a network or a portion of a network may include a wireless or cellular network, and the coupling may be a Code Division Multiple Access (CDMA) connection, a Global System for Mobile communications (GSM) connection, or other types of cel-lular or wireless coupling. In this example, the coupling may implement any of a variety of types of data transfer tech-nology, such as Single Carrier Radio Transmission Technol-ogy (1×RTT), Evolution-Data Optimized (EVDO) technol-ogy, General Packet Radio Service (GPRS) technology, Enhanced Data rates for GSM Evolution (EDGE) technol-ogy, third Generation Partnership Project (3GPP) including 3G, fourth-generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organi-zations, other long-range protocols, or other data transfer technology.

"Component" refers, for example, to a device, physical entity, or logic having boundaries defined by function or subroutine calls, branch points, APIs, or other technologies that provide for the partitioning or modularization of par-ticular processing or control functions. Components may be combined via their interfaces with other components to carry out a machine process. A component may be a packaged functional hardware unit designed for use with other com-ponents and a part of a program that usually performs a particular function of related functions. Components may constitute either software components (e.g., code embodied on a machine-readable medium) or hardware components.

A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application-specific integrated circuit (ASIC). A hardware component may also include programmable logic or circuitry that is temporarily config-ured by software to perform certain operations. For example, a hardware component may include software executed by a general-purpose processor or other programmable proces-sors. Once configured by such software, hardware compo-nents become specific machines (or specific components of a machine) uniquely tailored to perform the configured functions and are no longer general-purpose processors. It will be appreciated that the decision to implement a hard-ware component mechanically, in dedicated and perma-nently configured circuitry, or in temporarily configured circuitry (e.g., configured by software), may be driven by cost and time considerations. Accordingly, the phrase "hard-ware component" (or "hardware-implemented component") should be understood to encompass a tangible entity, be that an entity that is physically constructed, permanently con-figured (e.g., hardwired), or temporarily configured (e.g., programmed) to operate in a certain manner or to perform certain operations described herein.

Considering examples in which hardware components are temporarily configured (e.g., programmed), each of the hardware components need not be configured or instantiated at any one instance in time. For example, where a hardware component comprises a general-purpose processor config-ured by software to become a special-purpose processor, the general-purpose processor may be configured as respec-tively different special-purpose processors (e.g., comprising different hardware components) at different times. Software accordingly configures a particular processor or processors, for example, to constitute a particular hardware component at one instance of time and to constitute a different hardware component at a different instance of time. Hardware com-ponents can provide information to, and receive information from, other hardware components. Accordingly, the described hardware components may be regarded as being communicatively coupled. Where multiple hardware com-ponents exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein.

As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In other examples, the processors or processor-implemented components may be distributed across a number of geographic locations.

"Computer-readable storage medium" refers, for example, to both machine-storage media and transmission media. Thus, the terms include both storage devices/media and carrier waves/modulated data signals. The terms "machine-readable medium," "computer-readable medium," and "device-readable medium" mean the same thing and may be used interchangeably in this disclosure. "Ephemeral message" refers, for example, to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

"Machine storage medium" refers, for example, to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," and "computer-storage medium" mean the same thing and may be used interchangeably in this disclosure.

The terms "machine-storage media," "computer-storage media," and "device-storage media" specifically exclude carrier waves, modulated data signals, and other such media, at least some of which are covered under the term "signal medium." "Non-transitory computer-readable storage medium" refers, for example, to a tangible medium that is capable of storing, encoding, or carrying the instructions for execution by a machine. "Signal medium" refers, for example, to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

"User device" refers, for example, to a device accessed, controlled or owned by a user and with which the user interacts perform an action, or interaction on the user device, including interaction with other users or computer systems. "Carrier signal" refers to any intangible medium that is capable of storing, encoding, or carrying instructions for execution by the machine and includes digital or analog communications signals or other intangible media to facilitate communication of such instructions. Instructions may be transmitted or received over a network using a transmission medium via a network interface device. "Client device" refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network, and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth-generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

Components may constitute either software components (e.g., code embodied on a machine-readable medium) or hardware components. A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein.

Changes and modifications may be made to the disclosed examples without departing from the scope of the present disclosure. These and other changes or modifications are intended to be included within the scope of the present disclosure, as expressed in the following claims.

42

What is claimed is:

1. A method comprising:

accessing a collection of overt speech signals representing phonemes, phoneme sounds, words or phrases spoken at least partially using overt speech;

establishing a relationship between electromyograph (EMG) data corresponding to a first training set of overt speech segments, EMG data corresponding to a second training set of inner speech segments, and a third training set of rest data;

transforming, based on the relationship, the collection of overt speech signals into inner speech training data comprising EMG data representing inner speech corresponding to the phonemes, phoneme sounds, words or phrases spoken at least partially using the overt speech; and training a machine learning model to decode inner speech signals into a set of corresponding phonemes, phoneme sounds, words or phrases based on the inner speech training data.

2. The method of claim 1, further comprising:

selecting a portion of the inner speech training data comprising a set of EMG data representing inner speech corresponding to an individual word or phrase;

processing the set of EMG data of the portion of the inner speech training data by the machine learning model to predict a word or phrase corresponding to the portion of the set of EMG data;

computing a deviation between the predicted word or phrase and the individual word or phrase corresponding to the portion of the inner speech training data; and updating one or more parameters of the machine learning model based on the computed deviation.

3. The method of claim 1, further comprising:

obtaining the first training set of the overt speech segments corresponding to a training set of phonemes, phoneme sounds, words or phrases;

obtaining the second training set of the inner speech segments corresponding to the training set of phonemes, phoneme sounds, words or phrases; and obtaining the third training set of the rest data representing a portion when inner or overt speech signals are not being produced.

4. The method of claim 1, further comprising:

computing one or more transformation parameters based on the established relationship between the EMG data corresponding to the first training set of overt speech segments, the EMG data corresponding to the second training set of inner speech segments, and the third training set of rest data.

5. The method of claim 4, wherein transforming the collection of overt speech signals into the inner speech training data is based on the one or more transformation parameters.

6. The method of claim 3, further comprising:

retrieving the EMG data corresponding to the first training set of overt speech segments; and filtering the EMG data corresponding to the first training set of overt speech segments to remove drift and artifacts.

7. The method of claim 3, further comprising:

retrieving the EMG data corresponding to the second training set of inner speech segments; and filtering the EMG data corresponding to the second training set of inner speech segments to remove drift and artifacts.

8. The method of claim 3, further comprising:

processing the EMG data corresponding to the first training set of overt speech segments to tag time windows representing presence of speech activity;

processing the EMG data corresponding to the second training set of inner speech segments to tag time windows representing presence of speech activity;

validating the EMG data corresponding to the first training set of overt speech segments based on the tagged time windows of the first training set of overt speech segments; and validating the EMG data corresponding to the second training set of inner speech segments based on the tagged time windows of the second training set of inner speech segments.

9. The method of claim 8, wherein validating the EMG data corresponding to the first training set of overt speech segments comprises:

determining that a first portion of the EMG data corresponding to a first portion of the first training set of overt speech segments is between a first rest period and a second rest period; and in response to determining that the first portion of the EMG data is between the first rest period and the second rest period, marking the first portion of the first training set of overt speech segments as valid.

10. The method of claim 9, further comprising:

determining that a second portion of the EMG data corresponding to a second portion of the first training set of overt speech segments is during at least one of the first rest period or the second rest period; and in response to determining that the second portion of the EMG data is during at least one of the first rest period or the second rest period, marking the second portion of the first training set of overt speech segments as invalid.

11. The method of claim 8, wherein validating the EMG data corresponding to the second training set of inner speech segments comprises:

determining that a first portion of the EMG data corresponding to a first portion of the second training set of inner speech segments is between a first rest period and a second rest period; and in response to determining that the first portion of the EMG data is between the first rest period and the second rest period, marking the first portion of the second training set of inner speech segments as valid.

12. The method of claim 11, further comprising:

determining that a second portion of the EMG data corresponding to a second portion of the second training set of inner speech segments is during at least one of the first rest period or the second rest period; and in response to determining that the second portion of the EMG data is during at least one of the first rest period or the second rest period, marking the second portion of the second training set of inner speech segments as invalid.

13. The method of claim 11, wherein the second rest period is longer than the first rest period.

14. The method of claim 8, wherein presence of speech activity is detected by determining that a noise level in the EMG data corresponding to the first training set of overt speech segments is greater than a noise level associated with the third training set of rest data by a threshold amount.

15. The method of claim 3, further comprising:

computing a scaling parameter representing a ratio of the EMG data corresponding to the first training set of overt speech segments to the EMG data corresponding to the second training set of inner speech segments;

computing a colored noise parameter that matches a signal to noise (SNR) of the EMG data corresponding to the first training set of overt speech segments to the SNR of the EMG data corresponding to the second training set of inner speech segments based on a noise profile determined using the third training set of rest data; and computing a time shift parameter for stretching or compressing EMG data corresponding to overt speech.

16. The method of claim 15, further comprising:

adjusting the scaling parameter by a first random value drawn from a first specified range around a value of the scaling parameter;

adjusting the colored noise parameter by a second random value drawn from a second specified range around a value of the colored noise parameter; and adjusting the time shift parameter by a third random value drawn from a third specified range around a value of the time shift parameter.

17. The method of claim 16, further comprising:

modifying EMG data corresponding to the collection of overt speech signals using the adjusted scaling parameter, the adjusted colored noise parameter, and the adjusted time shift parameter to generate a first portion of the inner speech training data.

18. The method of claim 17, further comprising:

re-adjusting the scaling parameter, colored noise parameter, and the time shift parameter by additional random values drawn respectively from the first specified range, second specified range, and the third specified range; and modifying EMG data corresponding to the collection of overt speech signals using the re-adjusted scaling parameter, the re-adjusted colored noise parameter, and the re-adjusted time shift parameter to generate a second portion of the inner speech training data.

19. A system comprising:

at least one processor; and at least one memory component having instructions stored thereon that, when executed by the at least one processor, cause the at least one processor to perform operations comprising:

accessing a collection of overt speech signals representing phonemes, phoneme sounds, words or phrases spoken at least partially using overt speech;

establishing a relationship between electromyograph (EMG) data corresponding to a first training set of overt speech segments, EMG data corresponding to a second training set of inner speech segments, and a third training set of rest data;

transforming, based on the relationship, the collection of overt speech signals into inner speech training data comprising EMG data representing inner speech corresponding to the phonemes, phoneme sounds, words or phrases spoken at least partially using the overt speech; and training a machine learning model to decode inner speech signals into a set of corresponding phonemes, phoneme sounds, words or phrases based on the inner speech training data.

20. A non-transitory computer-readable storage medium having stored thereon instructions that, when executed by at least one processor, cause the at least one processor to perform operations comprising:

US 12,586,568 B2

45 accessing a collection of overt speech signals representing phonemes, phoneme sounds, words or phrases spoken at least partially using overt speech;

establishing a relationship between electromyograph (EMG) data corresponding to a first training set of overt 5 speech segments, EMG data corresponding to a second training set of inner speech segments, and a third training set of rest data;

transforming, based on the relationship, the collection of overt speech signals into inner speech training data 10 comprising EMG data representing inner speech corresponding to the phonemes, phoneme sounds, words or phrases spoken at least partially using the overt speech; and training a machine learning model to decode inner speech 15 signals into a set of corresponding phonemes, phoneme sounds, words or phrases based on the inner speech training data.

\* \* \* \* \*